US011478440B2

(12) United States Patent
Walczak et al.

(10) Patent No.: US 11,478,440 B2
(45) Date of Patent: Oct. 25, 2022

(54) COMBINATION OF ELAFIBRANOR OR DERIVATIVES THEREOF WITH AN ANTI-NASH, ANTI-FIBROTIC OR ANTI-CHOLESTATIC AGENT

(71) Applicant: GENFIT, Loos (FR)

(72) Inventors: Robert Walczak, Lille (FR); Carole Belanger, Bondues (FR); Vanessa Legry, Emmerin (FR); Benoît Noel, Gondecourt (FR); Emeline Descamps, Gondecourt (FR); Guillaume Vidal, Saint Andre Lez Lille (FR); Mathilde Walczak, Lille (FR)

(73) Assignee: GENFIT, Loos (FR)

( * ) Notice: Subject to any disclaimer, the term of this patent is extended or adjusted under 35 U.S.C. 154(b) by 0 days.

(21) Appl. No.: 16/606,233

(22) PCT Filed: Apr. 18, 2018

(86) PCT No.: PCT/EP2018/059967
§ 371 (c)(1),
(2) Date: Oct. 18, 2019

(87) PCT Pub. No.: WO2018/193006
PCT Pub. Date: Oct. 25, 2018

(65) Prior Publication Data
US 2020/0121625 A1    Apr. 23, 2020

(30) Foreign Application Priority Data

Apr. 18, 2017  (EP) .................................... 17305452
Feb. 13, 2018  (EP) .................................... 18305150

(51) Int. Cl.
| | | |
|---|---|---|
| A61K 31/192 | (2006.01) |
| A61P 1/16 | (2006.01) |
| A61K 31/166 | (2006.01) |
| A61K 31/198 | (2006.01) |
| A61K 31/426 | (2006.01) |
| A61K 31/437 | (2006.01) |
| A61K 31/4402 | (2006.01) |
| A61K 31/4439 | (2006.01) |
| A61K 31/506 | (2006.01) |
| A61K 31/519 | (2006.01) |
| A61K 31/52 | (2006.01) |
| A61K 31/53 | (2006.01) |
| A61K 31/538 | (2006.01) |
| A61K 31/575 | (2006.01) |
| A61K 31/662 | (2006.01) |
| A61K 31/194 | (2006.01) |
| A61K 31/438 | (2006.01) |
| A61K 31/444 | (2006.01) |
| A61K 31/5377 | (2006.01) |

(52) U.S. Cl.
CPC .......... *A61K 31/192* (2013.01); *A61K 31/166* (2013.01); *A61K 31/194* (2013.01); *A61K 31/198* (2013.01); *A61K 31/426* (2013.01); *A61K 31/437* (2013.01); *A61K 31/438* (2013.01); *A61K 31/4402* (2013.01); *A61K 31/444* (2013.01); *A61K 31/4439* (2013.01); *A61K 31/506* (2013.01); *A61K 31/519* (2013.01); *A61K 31/52* (2013.01); *A61K 31/53* (2013.01); *A61K 31/538* (2013.01); *A61K 31/5377* (2013.01); *A61K 31/575* (2013.01); *A61K 31/662* (2013.01); *A61P 1/16* (2018.01)

(58) Field of Classification Search
None
See application file for complete search history.

(56) References Cited

U.S. PATENT DOCUMENTS

| | | | |
|---|---|---|---|
| 8,772,342 B2 | 7/2014 | Darteil et al. |
| 2015/0352065 A1 | 12/2015 | Hanf et al. |
| 2016/0106793 A1 | 4/2016 | Peltier et al. |
| 2020/0206169 A1 | 7/2020 | Walczak et al. |

FOREIGN PATENT DOCUMENTS

| | | |
|---|---|---|
| WO | WO 2011/064350 | 6/2011 |
| WO | WO 2014/111584 | 7/2014 |
| WO | WO 2016/040860 | 3/2016 |
| WO | WO 2016/112305 | 7/2016 |
| WO | WO 2016/153948 | 9/2016 |
| WO | WO 2016/154258 | 9/2016 |
| WO | WO 2018/193007 | 10/2018 |

OTHER PUBLICATIONS

Fan, C. et al. "Metformin exerts anticancer effects through the inhibition of the Sonic hedgehog signaling pathway in breast cancer" *International Journal of Molecular Medicine*, 2015, pp. 204-214, vol. 36, No. 1.
Kinoh, H. et al. "Nanomedicines Eradicating Cancer Stem-like Cells in Vivo by pH-Triggered Intracellular Cooperative Action of Loaded Drugs" *ACS Nano*, 2016, pp. 5643-5655, No. 10, No. 6.
Anonymous: "Elafibranor Wikipedia version of Jan. 7, 2017" Jan. 7, 2017, XP055408806, Retrieved from the Internet: URL:https://en.wikipedia.org/w/index.php?title=Elafibranor&direction=next&oldid=756081267, retrieved on Sep. 21, 2017, pp. 1-5.
Written Opinion in International Application No. PCT/EP2018/059967, dated Sep. 12, 2018, pp. 1-13.

*Primary Examiner* — Samantha L Shterengarts
(74) *Attorney, Agent, or Firm* — Saliwanchik, Lloyd & Eisenschenk

(57) ABSTRACT

The present invention relates to a combination product and its use in therapy.

3 Claims, 17 Drawing Sheets
Specification includes a Sequence Listing.

A Experimental % inhibition

Cenicriviroc

| Bezafibrate [µM] | 0 | 0,31 | 0,6 | 1 | 2,50 | 5 | 10 |
|---|---|---|---|---|---|---|---|
| 0 | 0 | 0 | 0 | 0 | 0 | 0 | 0 |
| 1,25 | 0 | -11 | -9 | -3 | -17 | -2 | -3 |
| 2,5 | 0 | -15 | -17 | -10 | -10 | -8 | -11 |
| 5 | 0 | -5 | 7 | -7 | 2 | 5 | 5 |
| 10 | 0 | -13 | -9 | -3 | -13 | -10 | -4 |
| 20 | 0 | -12 | 0 | -2 | -6 | -6 | -3 |

% inhibition

Min — Max

B Excess over Bliss

Cenicriviroc

| Bezafibrate [µM] | 0 | 0,31 | 0,63 | 1,25 | 2,5 | 5 | 10 |
|---|---|---|---|---|---|---|---|
| 0 | - | - | - | - | - | - | - |
| 1,25 | - | -11 | -9 | -3 | -17 | -2 | -3 |
| 2,5 | - | -15 | -17 | -10 | -10 | -8 | -11 |
| 5 | - | -5 | 7 | -7 | 2 | 5 | 5 |
| 10 | - | -13 | -9 | -3 | -13 | -10 | -4 |
| 20 | - | -12 | 0 | -2 | -6 | -6 | -3 |

Total EOB score   -190

Min — Max

A. MSDC-0602

B. PXS-4728A (BI-1467335)

C. Apararenone

D. CF-102 (Namodenoson)

E. Vismodegib

F. PBI-4050

G. Emricasan

H. DUR-928

COMBINATION OF ELAFIBRANOR OR DERIVATIVES THEREOF WITH AN ANTI-NASH, ANTI-FIBROTIC OR ANTI-CHOLESTATIC AGENT

CROSS-REFERENCE TO RELATED APPLICATION

This application is the U.S. national stage application of International Patent Application No. PCT/EP2018/059967, filed Apr. 18, 2018.

STATEMENT REGARDING SEQUENCE LISTING

The Sequence Listing for this application is labeled "Seq-List.txt" which was created on May 16, 2022 and is 4637 bytes.

The present invention relates to a combination therapy for the treatment of inflammatory, metabolic, fibrotic and cholestatic diseases.

1-[4-methylthiophenyl]-3-[3,5-dimethyl-4-carboxydimethylmethyloxyphenyl]prop-2-en-1-one (Elafibranor, or ELA, formerly named GFT505), disclosed in WO2004005233, possesses properties which can be advantageous for the treatment of a number of gastroenterology and liver diseases, in particular cholestatic diseases such as PBC (primary biliary cholangitic) and PSC (primary sclerosing cholangitis), or liver diseases, in particular non-alcoholic fatty liver diseases (NAFLD) such as non-alcoholic steatoHepatitic (NASH).

Elafibranor has been tested for clinical efficacy in NASH in a 1-year liver biopsy-based Phase 2b trial (GFT505-212-7), one of the largest interventional studies ever conducted in NASH. Administered to over 800 patients and healthy volunteers to date, elafibranor has demonstrated beneficial properties for NASH, including in particular: improvement of markers of liver dysfunction, including ALAT, ASAT, γGT, ALP; improvement of insulin sensitivity and glucose homeostasis; favorable effects on plasma lipids, including decrease of plasma triglycerides and LDL-C, and increase of HDL-C levels; anti-inflammatory properties; efficacy on histological NASH parameters (steatosis, inflammation, fibrosis) in animal disease models and anti-fibrotic activities. The absence of safety concern has been confirmed in a full toxicological package up to 2-year carcinogenicity studies. Elafibranor is currently being evaluated in a clinical phase 3 study for the treatment of NASH. Evaluation of this molecule for the treatment of PBC in a clinical phase 2 study is also planned.

In view of its excellent therapeutic and pharmacological profile, elafibranor is a very promising molecule that could potentially be used in combined pharmacological approaches to target parallel or complementary key pathways involved in a high number of inflammatory, metabolic, fibrotic and cholestatic diseases.

SUMMARY OF INVENTION

The present invention relates to a combination product comprising:
(i) a PPAR agonist, in particular a compound of formula (I), or a pharmaceutically acceptable salt thereof:

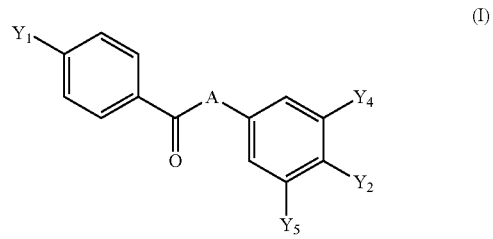

(I)

in which:
Y1 represents a halogen, a Ra, or Ga—Ra group;
A represents a CH=CH or a CH2-CH2 group;
Y2 represents a Gb-Rb group;
Ga and Gb, identical or different, represent an atom of oxygen or sulfur;
Ra represents a hydrogen atom, an unsubstituted (C1-C6)alkyl group, a (C6-C14)aryl group or a (C1-C6) alkyl group that is substituted by one or more halogen atoms, a (C1-C6)alkoxy or a (C1-C6)alkylthio group, (C3-C14)cycloalkyl groups, (C3-C14)cycloalkylthio groups or heterocyclic groups;
Rb represents a (C1-C6)alkyl group substituted by at least a —COORc group, wherein Rc represents a hydrogen atom, or a (C1-C6)alkyl group that is substituted or not by one or more halogen atoms, (C3-C14)cycloalkyl groups, or heterocyclic groups; and
Y4 and Y5, identical or different, representing a (C1-C6)alkyl group that is substituted or not by one or more halogen atoms, (C3-C14)cycloalkyl groups or heterocyclic groups
and
(ii) an anti-NASH, anti-fibrotic or anti-cholestatic agent.

In a particular embodiment of the compound of formula (I):
Y1 represents a halogen, a Ra, or a Ga—Ra group;
A represents a CH=CH group;
Y2 represents a Gb-Rb group;
Ga and Gb, identical or different, represent an atom of oxygen or sulfur;
Ra represents a (C1-C6)alkyl or (C3-C14)cycloalkyl group, in particular a (C1-C6)alkyl or (C3-C14)cycloalkyl group substituted or not by one or more halogen atoms;
Rb represents a (C1-C6)alkyl group substituted by a —COOR3 group, wherein Rc represents a hydrogen atom or an alkyl group having from one to four carbon atoms; and
Y4 and Y5 independently represent a (C1-C4)alkyl group.

In a particular embodiment of the compound of formula (I):
Y1 represents a Ra or Ga—Ra group;
A represents a CH2-CH2 group;
Y2 represents a Gb-Rb group;
Ga represents an atom of oxygen or sulfur and Gb represents an atom of oxygen;

Ra represents a (C1-C6)alkyl or (C3-C14)cycloalkyl group;
Rb represents a (C1-C6)alkyl group substituted by at least a —COORc group, wherein Rc represents a hydrogen atom or (C1-C4)alkyl group; and
Y4 and Y5 independently represent a (C1-C4)alkyl group.

In a particular embodiment of the compound of formula (I):
Y1 represents a halogen atom or a Ra or Ga—Ra group;
A represents a CH2-CH2 group;
Y2 represents a Gb-Rb group;
Ga represents an atom of oxygen or sulfur and Gb represents an atom of oxygen;
Ra represents a (C1-C6)alkyl or (C3-C14)cycloalkyl group that is substituted by one or more halogen atoms;
Rb represents a (C1-C6)alkyl group substituted or not by one or more halogen atoms and substituted by at least a —COORc group, wherein Rc represents a hydrogen atom or a (C1-C4)alkyl group; and
Y4 and Y5 represent a (C1-C4)alkyl group.

In a particular embodiment of the compound of formula (I), Gb is an oxygen atom and Rb is (C1-C6)alkyl group substituted by a —COORc group, wherein Rc represents a hydrogen atom or an unsubstituted linear or branched (C1-C4)alkyl group.

In a particular embodiment of the compound of formula (I), Y1 is a (C1-C6)alkylthio group that comprises a (C1-C6)alkyl group that is linear or branched that is substituted or not by one or more halogen atoms.

In a particular embodiment, the compound of formula (I) is selected in the group consisting of 1-[4-methylthiophenyl]-3-[3,5-dimethyl-4-carboxydimethylmethyloxy phenyl]prop-2-en-1-one (Elafibranor or GFT505), 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl] prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl] prop-2-en-1-one, 1-[4-trifluoromethyloxyphenyl]-3-[3,5-dimethyl-4-carboxydimethylmethyl oxyphenyl]prop-2-en-1-one, 2-[2,6-dimethyl-4-[3-[4-(methylthio)phenyl]-3-oxo-propyl]phenoxy]-2-methylpropanoic acid, and 2-[2,6-dimethyl-4-[3-[4-(methylthio) phenyl]-3-oxo-propyl]phenoxy]-2-methylpropanoic acid isopropyl ester.

In a particular embodiment of the invention, component (ii) is an anti-NASH agent. Illustrative, non-limiting, anti-NASH agents useful in the practice of the present invention include:
Acetyl-CoA carboxylase inhibitors;
Adenosine A3 receptor agonists;
Aldosterone antagonists and Mineralocorticoid antagonists;
AMP activated protein kinase stimulator;
Amylin receptor agonist and Calcitonin receptor agonists;
Angiopoietin-related protein-3 inhibitors;
Anti-LPS antibodies;
Apical sodium-codependent bile acid transporter inhibitors;
Betaine anhydrous or RM-003;
bioactive lipids;
Cannabinoid CB1 receptor antagonists;
Dual cannabinoid CB1 receptor/iNOS inhibitor;
Caspase inhibitors;
Cathepsin inhibitors;
CCR antagonists;
CCR3 chemokine modulators and eotaxin 2 ligand inhibitors;
Diacylglycerol-O-acyltransferase (DGAT) inhibitors;
Dipeptidyl peptidase IV (DPP4) inhibitors;
Insulin ligand and insulin receptor agonists;
Insulin sensitizer and MCH receptor-1 antagonist;
NOX (NADPH oxidase) inhibitors, such as dual NOX 1 and 4 inhibitors;
Extracellular matrix protein modulators;
Stearoyl CoA desaturase-1 inhibitors/fatty acid bile acid conjugates (FABAC);
Fatty Acid Synthase (FAS) Inhibitors;
Fibroblast Growth Factor 19 (FGF-19) receptor ligands, such as Recombinant Fibroblast Growth Factor 19 (FGF-19) protein, or functional engineered variant of the FGF-19 protein;
Fibroblast Growth Factor 21 (FGF-21) receptor ligands such as Fibroblast Growth Factor 21 (FGF-21) protein, or functional engineered variant of the FGF-21 protein;
Farnesoid X receptor (FXR) agonists;
Galectin 3 inhibitors;
Glucagon-like peptide-1 (GLP-1) analogs and GLP-1 receptor agonists;
G-protein coupled receptor (GPCR) modulators;
G-protein coupled receptor 84 antagonist, connective tissue growth factor ligand inhibitor and Free fatty acid receptor 1 agonists;
Hedgehog cell-signalling pathway inhibitors;
Integrin inhibitors;
ketohexokinase inhibitors Leukotriene (LT)/Phosphodiesterase (PDE)/Lipoxygenase (LO) inhibitors;
Lysyl oxidase homolog 2 inhibitors (LOXL2 inhibitors);
Macrolides;
Methyl CpG binding protein 2 modulator and Transglutaminase inhibitors;
miRNA antagonists;
Mitochondrial carrier family inhibitor and Mitochondrial phosphate carrier protein inhibitor;
Monoclonal antibodies;
Myeloperoxidase inhibitors;
mTOR modulators;
NAD-dependent deacetylase sirtuin stimulator; PDE 5 inhibitor;
Nicotinic Acid Receptor (GPR109) Agonists;
nuclear receptor ligands;
P2Y13 protein agonists;
Phenylalanine hydroxylase stimulators;
Protease-activated receptor (PAR)-2 antagonists;
Protein kinase modulators;
PPAR alpha agonists;
PPAR gamma agonists;
PPAR delta agonists;
PPAR alpha/gamma agonists;
PPAR alpha/delta agonists;
PPAR gamma/delta;
PPAR alpha/gamma/delta agonists or PPAR pan-agonists;
Rho-associated protein kinase 2 (ROCK2) inhibitors;
Sodium-GLucose Transport (SGLT) 1 inhibitors;
Sodium-glucose transport (SGLT) 2 inhibitors;
Stearoyl-CoA desaturase-1 inhibitors;
signal-regulating kinase 1 (ASK1) inhibitors;
thyroid receptor β (THR β) agonists;
Toll Like Receptor 2 (TLR-2) antagonists;
Toll Like Receptor 4 (TLR-4) antagonists;

Type I natural killer T cells inhibitors;
Tyrosine kinase receptor (RTK) modulators;
Urate anion exchanger 1 inhibitors and Xanthine oxidase inhibitors;
Vascular adhesion protein-1 (VAP-1) inhibitors; and
Vitamin D receptor (VDR) agonists.

In a further particular embodiment of the invention, component (ii) is an anti-NASH agent.

In a particular embodiment, the anti-NASH agent is selected from:
Acetyl-CoA carboxylase inhibitors;
Anti-LPS antibodies;
Apical sodium-codependent bile acid transporter inhibitors;
bioactive lipids;
Cannabinoid CB1 receptor antagonists;
Dual cannabinoid CB1 receptor/iNOS inhibitor;
Caspase inhibitors;
Cathepsin inhibitors;
CCR antagonists;
Diacylglycerol-O-acyltransferase (DGAT) inhibitors;
Dipeptidyl peptidase IV (DPP4) inhibitors;
NOX (NADPH oxidase) inhibitors, such as dual NOX 1 and 4 inhibitors;
Extracellular matrix protein modulators;
Stearoyl CoA desaturase-1 inhibitors/fatty acid bile acid conjugates (FABAC);
Fibroblast Growth Factor 19 (FGF-19) receptor ligands, such as Recombinant Fibroblast Growth Factor 19 (FGF-19) protein, or functional engineered variant of the FGF-19 protein; Fibroblast Growth Factor 21 (FGF-21) receptor ligands such as Fibroblast Growth Factor 21 (FGF-21) protein, or functional engineered variant of the FGF-21 protein;
Farnesoid X receptor (FXR) agonists;
Galectin 3 inhibitors;
Glucagon-like peptide-1 (GLP-1) analogs;
G-protein coupled receptor (GPCR) modulators;
Integrin inhibitors;
Leukotriene (LT)/Phosphodiesterase (PDE)/Lipoxygenase (LO) inhibitors;
Macrolides;
miRNA antagonists;
Monoclonal antibodies;
mTOR modulators;
nuclear receptor ligands;
P2Y13 protein agonists;
Protease-activated receptor (PAR)-2 antagonists;
Protein kinase modulators;
PPAR alpha agonists;
PPAR gamma agonists;
PPAR delta agonists;
PPAR alpha/gamma agonists;
PPAR alpha/delta agonists;
PPAR gamma/delta;
PPAR alpha/gamma/delta agonists or PPAR pan-agonists;
Rho-associated protein kinase 2 (ROCK2) inhibitors;
Sodium-glucose transport (SGLT) 2 inhibitors;
signal-regulating kinase 1 (ASK1) inhibitors;
thyroid receptor β (THR β) agonists;
Toll Like Receptor 4 (TLR-4) antagonists;
Tyrosine kinase receptor (RTK) modulators;
Vascular adhesion protein-1 (VAP-1) inhibitors; and
Vitamin D receptor (VDR) agonists.

Other anti-NASH agents include KB-GE-001 and NGM-386 and NGM-395, NC-10, and TCM-606F. Further anti-NASH agents include icosabutate, NC-101, NAIA-101 colesevelam, and PRC-4016.

In a particular embodiment of the invention, component (ii) is an anti-fibrotic agent. Illustrative, non-limiting, anti-fibrotic agents useful in the practice of the present invention include:
Adenosine A3 receptor agonists;
Angiotensin II receptor blockers;
antisense oligonucleotides targeting transforming growth factor beta 2 (TGF-β2);
Bioactive lipids;
Caspase inhibitors;
Cannabinoid CB2 receptor mimetics;
Dual Farnesoid X receptor (FXR)/TGR5 agonists;
NOX (NADPH oxidase) inhibitors, such as dual NOX 1 and 4 inhibitors;
Galectin 3 inhibitors;
Hedgehog cell-signalling pathway inhibitors;
Immunomodulators;
Integrin inhibitors;
Macrophage mannose receptor modulators;
Metalloprotease-9 (MMP-9) stimulators;
Monoclonal antibodies;
NF-kappa B inhibitors;
Non-Steroid Anti-Inflammatory Drugs (NSAIDs);
PDGFR modulators;
PPAR alpha agonists;
PPAR gamma agonists;
PPAR delta agonists;
PPAR alpha/gamma agonists;
PPAR alpha/delta agonists;
PPAR gamma/delta; and
PPAR alpha/gamma/delta agonists or PPAR pan-agonists.

In a further particular embodiment the anti-fibrotic agent is selected in the group consisting of:
antisense oligonucleotides targeting transforming growth factor beta 2 (TGF-β2);
Bioactive lipids;
Caspase inhibitors;
Cannabinoid CB2 receptor mimetics;
Dual Farnesoid X receptor (FXR)/TGR5 agonists;
NOX (NADPH oxidase) inhibitors, such as dual NOX 1 and 4 inhibitors;
Galectin 3 inhibitors;
Immunomodulators;
Integrin inhibitors;
Macrophage mannose receptor modulators;
Metalloprotease-9 (MMP-9) stimulators;
Monoclonal antibodies;
NF-kappa B inhibitors;
Non-Steroid Anti-Inflammatory Drugs (NSAIDs);
PDGFR modulators;
PPAR alpha agonists;
PPAR gamma agonists;
PPAR delta agonists;
PPAR alpha/gamma agonists;
PPAR alpha/delta agonists;
PPAR gamma/delta; and
PPAR alpha/gamma/delta agonists or PPAR pan-agonists.

Other anti-fibrotic agents include HEC-585, INV-240, RNAi therapeutic (Silence Therapeutics) and SAMiRNA program (Bioneer Corp).

Other illustrative antifibrotic agents include pirfenidone or receptor tyrosine kinase inhibitors (RTKIs) such as Nintedanib, Sorafenib and other RTKIs, or angiotensin II (AT1)

receptor blockers, or CTGF inhibitor, or any antifibrotic compound susceptible to interfere with the TGFβ and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ.

In a particular embodiment of the invention, component (ii) is an anti-cholestatic agent. Illustrative, non-limiting, anti-cholestatic agents useful in the practice of the present invention include:

apical sodium-codependent bile acid transporter inhibitors (ASBTi);
Bile acids;
cathepsin inhibitors;
CCR antagonists;
CD40 inhibitors;
CD80 inhibitors;
NOX (NADPH oxidase) inhibitors, such as dual NOX 1 and 4 inhibitors;
Farnesoid X receptor (FXR) agonists;
Fibroblast Growth Factor (FGF) 19 recombinant;
Fractalkine ligand inhibitors;
ileal sodium bile acid cotransporter inhibitors;
Monoclonal antibodies;
PPAR alpha agonists;
PPAR gamma agonists;
PPAR delta agonists;
PPAR alpha/gamma agonists;
PPAR alpha/delta agonists;
PPAR gamma/delta; and
PPAR alpha/gamma/delta agonists or PPAR pan-agonists.

In a particular embodiment, the anti-cholestatic agent is selected in the group consisting of:

apical sodium-codependent bile acid transporter inhibitors (ASBTi);
Bile acids;
cathepsin inhibitors;
CCR antagonists;
CD40 inhibitors;
CD80 inhibitors;
NOX (NADPH oxidase) inhibitors;
Farnesoid X receptor (FXR) agonists;
Fibroblast Growth Factor (FGF) 19 recombinant;
Fractalkine ligand inhibitors;
ileal sodium bile acid cotransporter inhibitors;
Monoclonal antibodies;
PPAR alpha agonists;
PPAR gamma agonists;
PPAR delta agonists;
PPAR alpha/gamma agonists;
PPAR alpha/delta agonists;
PPAR gamma/delta;
PPAR alpha/gamma/delta agonists or PPAR pan-agonists.

Illustrative acetyl-CoA carboxylase inhibitors include, but are not limited to GS-0976, ND-654, AC-8632, PF05221304, CP640186, Gemcabene, MK-4074, and PF05175157.

Illustrative adenosine A3 receptor agonists include but are not limited to 2-(1-Hexynyl)-N-methyladenosine, Piclidenoson CF-101 (IB-MECA), Namodenoson CF-102, 2-CI-IB-MECA, CP-532,903, Inosine, LUF-6000, and MRS-3558.

Illustrative aldosterone antagonists and mineralocorticoid receptor antagonists include, but are not limited to, Apararenone (MT 3995), Amiloride, Spironolactone, Eplerenone, Canrenone and potassium canrenoate, progesterone, drospirenone, gestodene, and benidipine.

Illustrative AMP activated protein kinase stimulators include, but are not limited to PXL-770, MB-11055 Debio-0930B metformin, CNX-012, O-304, mangiferin calcium salt, eltrombopag, carotuximab, and Imeglimin.

Illustrative Amylin receptor agonist and Calcitonin receptor agonists include, but are not limited to, KBP-042 and KBP-089.

Illustrative angiopoietin-related protein-3 inhibitors include, but are not limited to ARO-ANG3, IONIS-ANGGPTL3-LRx or AKCEA-ANGPTL3LRx, evinacumab, and ALN-ANG.

According to the invention, the term "angiotensin type 1 receptor antagonists" as used herein includes, but is not limited to, Irbesartan.

According to the invention, the term "anti-LPS antibodies" as used herein includes, but is not limited to IMM-124-E.

Illustrative antisense oligonucleotide targeting transforming growth factor beta 2 include, but are not limited to ASPH-0047, IMC-TR1 and ISTH-0047.

Illustrative apical sodium-codependent bile acid transporter inhibitor include, but are not limited to A-4250, volixibat, maralixibat formerly SHP-625, GSK-2330672, elobixibat and CJ-14199.

Illustrative bile acids include, but are not limited to obeticholic acid (OCA) and UDCA, norursodeoxycholic acid, and ursodiol.

Illustrative bioactive lipids include, but are not limited to 5-hydroxyeicosapentaenoic acid (15-HEPE, DS-102).

In a further particular embodiment, the bioactive lipid may be selected from unsaturated fatty acids such as 25 arachidonic acid, icosapentethyl ester, eicosapentaneoic acid, and docosahexaenoic acid.

Illustrative cannabinoid CB1 receptor antagonists include, but are not limited to namacizumab, GRC-10801, MRI-1569, MRI-1867, DBPR-211, AM-6527:AM-6545, NESS-11-SM, CXB-029, GCC-2680, TM-38837, Org-50189, PF-514273, BMS-812204, ZYO-1, AZD-2207, AZD-1175, otenabant, ibipinabant, surinabant, rimonabant, drinabant, SLV-326, V-24343, and O-2093.

Illustrative cannabinoid CB2 receptor mimetics include, but are not limited to anabasum (Resunab, JKT-101).

Illustrative caspase inhibitors include, but are not limited to emricasan, belnacasan, nivocasan, IDN-7314, F-573, VX-166, YJP-60107, MX-1122, IDN-6734, TLC-144, SB-234470, IDN-1965, VX-799, SDZ-220-976, and L-709049.

Illustrative cathepsin inhibitors include, but are not limited to VBY-376, VBY-825, VBY-036, VBY-129, VBY-285, Org-219517, LY3000328, RG-7236, and BF/PC-18.

Illustrative CCR antagonists include, but are not limited to CCR2/5 antagonists such as cenicriviroc; PG-092, RAP-310, INCB-10820, RAP-103, PF-04634817, and CCX-872.

Illustrative CD40 inhibitors include, but are not limited to FFp-104, xl-050, DOM-0800, XmAb-5485, KGYY-15, FFP-106, TDI-0028, and ABI-793.

Illustrative CD80 inhibitors include, but are not limited to RhuDex, FPT-155, ToleriMab, galiximab, SCH-212394, IGM-001, ASP-2408, and SCH-204698.

Illustrative CCR3 chemokine modulators and eotaxin 2 ligand inhibitors include, but are not limited to bertilimumab, CM-101 (humanized), CM-102, and RNS-60.

Illustrative diacylglycerol-O-acyltransferase inhibitors include, but are not limited to IONIS-DGAT2Rx (formerly ISIS-DGAT2Rx), LY-3202328, BH-03004, KR-69530, OT-13540, AZD-7687, PF-06865571, PF-06424439, and ABT-046.

Illustrative dipeptidyl peptidase IV inhibitors include, but are not limited to evogliptin, vidagliptin, fotagliptin, alogliptin, saxagliptin, tilogliptin, anagliptin, sitagliptin, retagliptin, melogliptin, gosogliptin, trelagliptin, teneligliptin, dutogliptin, linagliptin, gemigliptin, yogliptin, betagliptin, imigliptin, omarigliptin, vidagliptin, and denagliptin.

Illustrative Fatty Acid Synthase (FAS) inhibitors include, but are not limited to TVB-2640; TVB-3664; TVB-3166, TVB-3150, TVB-3199, TVB-3693BZL-101, 2-octadecynoic acid, MDX-2, Fasnall, MT-061, G28UCM, MG-28, HS-160, GSK-2194069, KD-023, cilostazol.

In a particular embodiment, the FAS inhibitor is a compound selected in the following list of compounds:

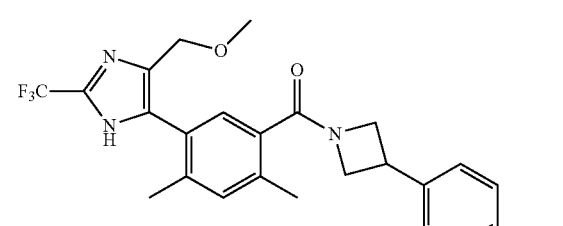

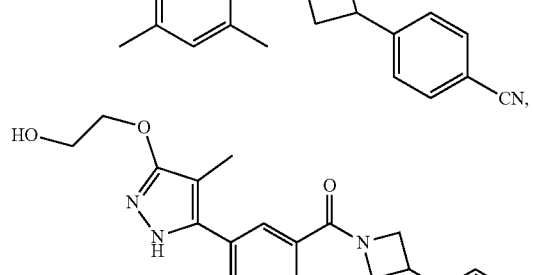

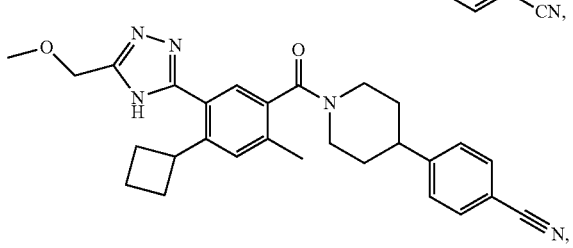

-continued

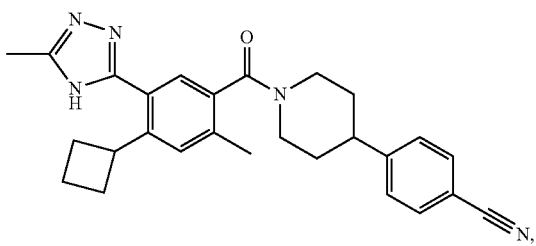

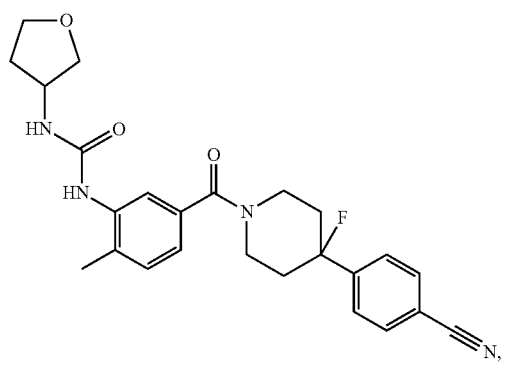

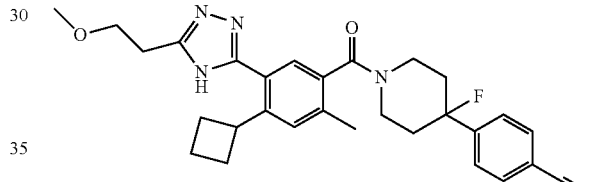

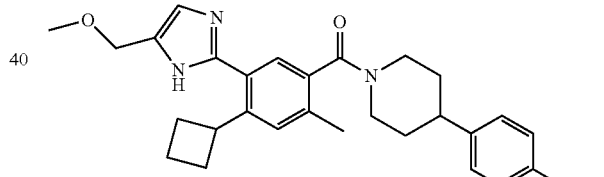

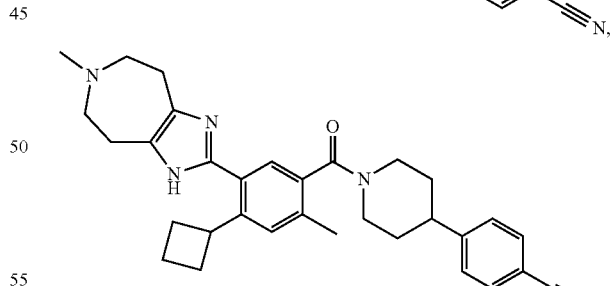

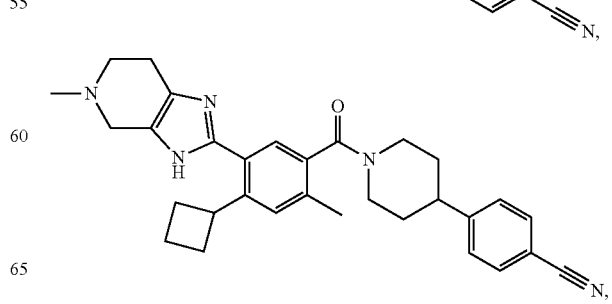

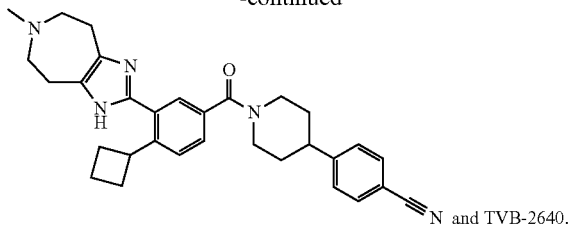
N and TVB-2640.

In another particular embodiment, the FAS inhibitor is selected from:

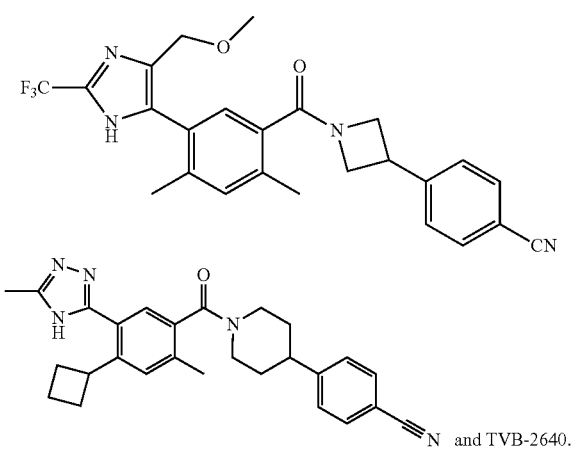
N and TVB-2640.

In a particular embodiment, the FAS inhibitor is TVB-2640.

Illustrative dual Farnesoid X receptor (FXR)/TGR5 agonists include, but are not limited to INT-767.

Illustrative NOX (NADPH oxidase) inhibitors include, but are not limited to, dual NOX 1&4 inhibitors; GKT-831 (2-(2-chlorophenyl)-4-[3-(dimethylamino)phenyl]-5-methyl-1H-pyrazolo[4,3-c]pyridine-3,6(2H,5H)-dione), formerly GKT137831 and GKT-901.

Illustrative extracellular matrix protein modulators include, but are not limited to CNX-024, CNX-025 and SB-030.

Illustrative Farnesoid X receptor (FXR) agonists includes but are not limited to obeticholic acid (OCA), GS-9674, LJN-452 or LJN452, LMB763, EDP-305, AKN-083, INT-767, GNF-5120, LY2562175, INV-33, NTX-023-1, EP-024297, Px-103 and SR-45023.

Illustrative Fractalkine ligand inhibitors include, but are not limited to E-6011 and KAN-0440567.

Illustrative Fibroblast Growth Factor 19 (FGF-19) receptor ligand, Recombinant Fibroblast Growth Factor 19 (FGF-19) protein or functional engineered variant of FGF-19 include, but are not limited to NGM-282.

Illustrative Fibroblast Growth Factor 21 (FGF-21) receptor ligand, Fibroblast Growth Factor 21 (FGF-21) protein, include, but are not limited to PEG-FGF21 (formerly BMS-986036), YH-25348, BMS-986171, YH-25723, LY-3025876 and NNC-0194-0499.

Illustrative Galectin 3 inhibitors include, but are not limited to GR-MD-02, TD-139, ANG-4021, Galectin-3C, LJPC-201, TFD-100, GR-MD-03, GR-MD-04, GM-MD-01, GM-CT-01, GM-CT-02, Gal-100 and Gal-200.

Illustrative Glucagon-like peptide-1 (GLP-1) analogs include, but are not limited to semaglutide, liraglutide, exenatide, albiglutide, dulaglutide, lixisenatide, loxenatide, efpeglenatide, taspoglutide, MKC-253, DLP-205 and ORMD-0901.

Illustrative Glucagon-like peptide-1 (GLP-1) receptor agonists include, but are not limited to LY-3305677, and Oxyntomodulin long acting.

Illustrative G-protein coupled receptor (GPCR) modulators include, but are not limited to CNX-023.

Illustrative G-protein coupled receptor 84 antagonist (GPR84 antagonist), connective tissue growth factor ligand inhibitor and Free fatty acid receptor 1 agonist (FFAR1 agonist) include, but are not limited to, PBI-4050, PBI-4265, PBI-4283, and PBI-4299.

Illustrative Hedgehog cell-signalling pathway inhibitors include, but are not limited to Vismodegib, TAK-441, IPI-926, Saridegib, Sonidegib/Erismodegib, BMS-833923/XL139, PF-04449913, Taladegib/LY2940680, ETS-2400, SHR-1539, and CUR61414.

Illustrative ileal sodium bile acid cotransporter inhibitors include, but are not limited to A-4250, GSK-2330672, volixibat, CJ-14199, and elobixibat.

Illustrative immunomodulators include, but are not limited to PBI-4050, PBI-4265, PBI-4283, PBI-4299 and AIC-649.

Illustrative Insulin sensitizer and MCH receptor-1 antagonist include but are not limited to MSDC-0602k, MSDC-0602, CSTI-100 and AMRI.

Illustrative integrin inhibitors include, but are not limited to integrin inhibitors of Pliant Therapeutic, integrin inhibitors of Indalo Therapeutics, integrin inhibitors of St Louis University, ProAgio, and GSK-3008348.

Illustrative ketohexokinase inhibitors include, but are not limited to, JNJ-28165722; JNJ-42065426; JNJ-42152981; JNJ-42740815; JNJ-42740828, and PF-06835919.

Illustrative leukotriene/phosphodiesterase/lipoxygenase inhibitors include, but are not limited to tipelukast (formerly MN-001), tomelukast, sulukast, masilukast, zafirlukast, pranlukast, montelukast, gemilukast, verlukast, aklukast, pobilikast, cinalukast, and iralukast.

Illustrative Lysyl oxidase homolog 2 inhibitors include, but are not limited to, Rappaport, InterMune, Pharmaxis, AB-0023, Simtuzumab, PXS-5382A, and PXS-5338.

Illustrative macrolides include, but are not limited to solithromycin, azithromycin, and erythromycin.

Illustrative macrophage mannose receptor modulators include, but are not limited to AB-0023, MT-1001, [18F] FB18mHSA, Xemys, technetium Tc 99m tilmanocept, and CDX-1307.

Illustrative methyl CpG binding protein 2 modulator and transglutaminase inhibitors include, but are not limited to, cysteamine, EC Cysteamine, enteric-coated cysteamine bitartrate, cysteamine bitartrate (enteric-coated), Bennu, cysteamine bitartrate (enteric-coated), Raptor, cysteamine bitartrate, DR Cysteamine, delayed release enteric coated cysteamine bitartrate, mercaptamine, mercaptamine (enteric-coated), Bennu, mercaptamine (enteric-coated), Raptor, RP-103, RP-104, PROCYSBI, and mercaptamine (enteric-coated).

Illustrative miRNA antagonists include, but are not limited to RG-125 (formerly AZD4076), RGLS-5040, RG-101, MGN-5804, and MRG-201.

Illustrative metalloprotease-9 (MMP-9) stimulators include, but are not limited to MMP-9 stimulator of Elastomics Ab.

Illustrative mitochondrial carrier family inhibitor and Mitochondrial phosphate carrier protein inhibitor include, but are not limited to TRO-19622, Trophos, olesoxime, RG-6083, or RO-7090919.

Illustrative myeloperoxidase inhibitors include, but are not limited to PF-06667272.

Illustrative monoclonal antibodies (mAbs) include, but are not limited to bertilimumab, NGM-313, IL-20 targeting mAbs, fresolimumab (antiTGFβ) (formerly GC1008), timolumab formerly BTT-1023, namacizumab, omalizumab, ranibizumab, bevacizumab, lebrikizumab, epratuzumab, felvizumab, matuzumab, monalizumab, reslizumab, foralumab (NI-0401, anti-CD3), simtizumab (GS-6624) mAb against LOXL2, ustekinumab, an anti-TNF antibody, and inebilizumab.

Illustrative monoclonal antibodies are selected in the group consisting of anti-IL20 mAbs, anti-TGFβ antibodies, anti-CD3 antibodies, anti-LOXL2 antibodies and anti-TNF antibodies.

Illustrative mTOR modulators include, but are not limited to MSDC-0602 and AAV gene therapy co-administered with SVP-sirolimus.

Illustrative NAD-dependent deacetylase sirtuin stimulator; PDE 5 inhibitor include, but are not limited to NS-0200.

Illustrative NF-kappa B inhibitors include, but are not limited to LC-280126.

Illustrative Nicotinic Acid Receptor (GPR109) Agonists include, but are not limited to ARI-3037MO, MMF, LUF 6283, Acifran, IBC 293, MK-1903, GSK256073, MK-6892, MK-0354, SLx-4090, lomitapide, lexibulin, apabetalone, acifran, laropiprant, daporinad, anacetrapib, INCB-19602, ST-07-02, lomefloxacin, Niacin, and controlled release/laropiprant.

Illustrative non-steroid anti-inflammatory drugs (NSAIDs) include, but are not limited to F-351, salicylates (aspirin), acetaminophen, propionic acid derivatives (ibuprofen, naproxen), acetic acid derivatives (indomethacin, diclofenac), enolic acid derivatives (piroxicam, phenylbutazone), anthranilic acid derivatives (meclofenalmic acid, flufenamic acid), selective COX-2 inhibitors (celecoxib, parecoxib), and sulfonanilides (nimesulide).

Illustrative nuclear receptor ligands include, but are not limited to DUR-928 (formerly DV 928).

Illustrative P2Y13 protein agonists include, but are not limited to CER-209.

Illustrative PDGFR modulators include, but are not limited to BOT-501 and BOT-191.

Illustrative phenylalanine hydroxylase stimulators include, but are not limited to Pegvaliase, sapropterin, AAV-PAH, CDX-6114, sepiapterin, RMN-168, ALTU-236, ETX-101, HepaStem, rolipram, and alprostadil.

Illustrative PPAR alpha agonists include, but are not limited to fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, and SR10171.

Illustrative PPAR gamma agonists include, but are not limited to, Pioglitazone, deuterated pioglitazone, Rosiglitazone, efatutazone, ATx08-001, OMS-405, CHS-131, THR-0921, SER-150-DN, KDT-501, GED-0507-34-Levo, CLC-3001, and ALL-4.

Illustrative PPAR delta agonists include, but are not limited to GW501516 (Endurabol or ({4-[({4-methyl-2-[4-(trifluoromethyl)phenyl]-1,3-thiazol-5-yl}methyl)sulfanyl]-2-methylphenoxy}acetic acid)), MBX8025 (Seladelpar or {2-methyl-4-[5-methyl-2-(4-trifluoromethyl-phenyl)-2H-[1,2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy]acetic acid), L165041, HPP-593, and NCP-1046.

Illustrative PPAR alpha/gamma agonists (also named glitazars) include, but are not limited to Saroglitazar, Aleglitazar, Muraglitazar, Tesaglitazar, and DSP-8658.

In addition to elafibranor, illustrative PPAR alpha/delta agonists include, without limitation, T913659.

Illustrative PPAR gamma/delta agonist include, but are not limited to a conjugated linoleic acid (CLA) and T3D-959.

Illustrative PPAR alpha/gamma/delta agonists or "PPAR pan-agonists", include, but are not limited to IVA337 (Lanifibranor), TTA (tetradecylthioacetic acid), Bavachinin, GW4148, GW9135, Bezafibrate, Lobeglitazone and CS038.

Illustrative protease-activated receptor (PAR)-2 antagonists include, but are not limited to PZ-235 and NP-003.

Illustrative protein kinase modulators include, but are not limited to CNX-014, MB-11055, ALF-1, mangiferin, amlexanox, GS-444217, REG-101 and valine.

Illustrative Rho-associated protein kinase 2 (ROCK2) inhibitors include, but are not limited to KD-025, TRX-101, BA-1049, LYC-53976, INS-117548 and RKI-1447.

Illustrative signal-regulating kinase 1 (ASK1) inhibitors include, but are not limited to selonsertib (formerly GS-4997).

Illustrative sodium-glucose transport (SGLT) 1 inhibitors include, but are not limited to LX-4212/LX-4211/sotagliflozin, SAR-439954, LIK-066 (Licoglifozin), LX-2761, GSK-161235, LP-925219, KGA-2727, SAR-7226, SAR-474832, SY-008, and AVX-3030.

Illustrative sodium-glucose transport (SGLT) 2 inhibitors include, but are not limited to remogliflozin, dapagliflozin, empagliflozin, ertugliflozin, sotagliflozin, ipragliflozin, tianagliflozin, canagliflozin, tofogliflozin, janagliflozin, bexagliflozin, luseogliflozin, sergliflozin, HEC-44616, AST-1935 and PLD-101.

Illustrative stearoyl CoA desaturase-1 inhibitors/fatty acid bile acid conjugates include, but are not limited to aramchol, GRC-9332, steamchol, TSN-2998, GSK-1940029 and XEN-801.

Illustrative thyroid hormone receptor β (THR β) agonists include, but are not limited to VK-2809, MGL-3196, MGL-3745, SKL-14763, sobetirome, BCT-304, ZYT-1, MB-07811 and eprotirome.

Illustrative Toll Like Receptor 2 and 4 (TLR-2) antagonists include, but are not limited to CI-201 also known as VB-201.

Illustrative Toll Like Receptor 4 (TLR-4) antagonists include, but are not limited to naltrexone, JKB-121 also known as Nalmefene, M-62812, resatorvid, dendrophilin, CS-4771, AyuV-1, AyuV-25, NI-0101, EDA-HPVE7 and eritoran.

Illustrative Type I natural killer T cells inhibitors include but are not limited to GRI-0621.

Illustrative Receptor tyrosine kinase (RTK) modulators include, but are not limited to CNX-025, KBP-7018, nintedanib and sorafenib.

Illustrative urate anion exchanger 1 inhibitors and xanthine oxidase inhibitors include, but are not limited to, lesinurad, RLBN-1001, verinurad, KUX-1151, and lesinurad+allopurinol.

Illustrative vascular adhesion protein-1 (VAP-1) inhibitors also named Amine Oxidase Copper containing 2 (AOC3), include, but are not limited to BI-1467335 formerly PXS-4728A, CP-664511, PRX-167700, ASP-8232, RTU-1096, RTU-007 and BTT-1023.

Illustrative vitamin D receptor (VDR) agonists include, but are not limited to calciferol, alfacalcidol, 1,25-dihydroxyvitamin D3, Vitamin D2, Vitamin D3, calcitriol, Vitamin D4, Vitamin D5, dihydrotachysterol, calcipotriol, tacalcitol 1,24-dihydroxyvitamin D3 and paricalcitol.

According to the present invention, the term "PPAR(s) agonists" refers the Peroxisome Proliferator Activated Receptor agonists, which are a class of drugs which plays a central role in lipid and glucose homeostasis. PPARα mainly influences fatty acid metabolism and its activation lowers lipid levels, while PPARγ is mostly involved in the regulation of the adipogenesis, energy balance, and lipid biosynthesis. PPARδ participates in fatty acid oxidation, mostly in skeletal and cardiac muscles, but it also regulates blood glucose and cholesterol levels.

In a more particular embodiment, the compound of formula (I) is Elafibranor, or a pharmaceutically acceptable salt thereof.

In a particular embodiment of the combination product of the invention:
component (i) is Elafibranor or a pharmaceutically acceptable salt thereof; and
component (ii) is selected from GKT-831, aramchol, SHP-625, emricasan, saroglitazar, IMM-124-E, GS-9674, NGM-282, A-4250, GR-MD-02, GS-4997, F-351, solithromycin, remogliflozin, BTT-1023, IVA-337 (Lanifibranor), JKB-121 (Nalmefene), KD-025, MSDC-0602 or MSDC-0602k, PBI-4050, PEG-FGF21, tipelukast, VK-2809, MGL-3196, GS-0976, RG-125, volixibat, pioglitazone, semaglutide, GSK2330672, MBX-8025, CP-640186, Selonsertib, GKT-831, PXS-4728A, Vismodegib, CF-102 (Namodenoson), MT-3995 (Aparanerone), icosapentethyl ester, KD-025, DUR-928, and Gemcabene, in particular Selonsertib, GKT-831, PXS-4728A, Aramchol, PBI-4050, MSDC-0602k, VK-2809, MGL-3196, Vismodegib, CF-102 (Namodenoson), MT-3995 (Aparanerone), JKB-121 (Nalmefene), emricasan, KD-025, and DUR-928.

In a particular embodiment of the combination product of the invention:
component (i) is Elafibranor or a pharmaceutically acceptable salt thereof; and
component (ii) is selected from GKT-831, aramchol, SHP-625, emricasan, saroglitazar, IMM-124-E, GS-9674, NGM-282, A-4250, GR-MD-02, GS-4997, LJN-452, F-351, solithromycin, remogliflozin, BTT-1023, IVA-337 (Lanifibranor), JKB-121, KD-025, MSDC-0602, PBI-4050, PEG-FGF21, tipelukast, VK-2809, MGL-3196, GS-0976, pentasa, RG-125, volixibat, pioglitazone, ursodeoxycholic acid, semaglutide, GSK2330672, and MBX-8025, in particular from aramchol, SHP-625, emricasan, saroglitazar, IMM-124-E, GS-9674, NGM-282, A-4250, GR-MD-02, GS-4997, LJN-452, F-351, solithromycin, remogliflozin, BTT-1023, IVA-337 (Lanifibranor), JKB-121, KD-025, MSDC-0602, PBI-4050, PEG-FGF21, tipelukast, VK-2809, MGL-3196, GS-0976, RG-125, volixibat, pioglitazone, ursodeoxycholic acid, semaglutide, GSK2330672, and MBX-8025.

In a particular embodiment of the combination product of the invention:
component (i) is Elafibranor or a pharmaceutically acceptable salt thereof; and
component (ii) is selected from GKT-831, aramchol, SHP-625, emricasan, saroglitazar, IMM-124-E, GS-9674, NGM-282, A-4250, GR-MD-02, GS-4997, F-351, solithromycin, remogliflozin, BTT-1023, IVA-337 (Lanifibranor), JKB-121, KD-025, MSDC-0602, PBI-4050, PEG-FGF21, tipelukast, VK-2809, MGL-3196, GS-0976, pentasa, RG-125, volixibat, pioglitazone, semaglutide, GSK2330672, and MBX-8025.

In a particular embodiment, the combination product is a combination of ELA and GKT-831, ELA and Selonsertib, ELA and GS-0976 or ELA and Pentasa.

In a particular embodiment, the combination product is a combination of ELA and GS-0976, ELA and CP-640186, ELA and Selonsertib, ELA and GKT-831 (formerly GKT137831), ELA and BI-1467335/PXS-4728A, ELA and Aramchol, ELA and PBI-4050, ELA and MSDC-0602k, ELA and VK-2809, ELA and MGL-3196, ELA and Vismodegib, ELA and CF-102 (Namodenoson), ELA and MT-3995 (Aparanerone), ELA and JKB-121 (Nalmefene), ELA and Emricasan, ELA and KD-025, ELA and DUR-928, or ELA and Gemcabene.

In a particular embodiment, the combination product is a combination of ELA and Selonsertib, ELA and GKT-831 (formerly GKT137831), ELA and BI-1467335/PXS-4728A, ELA and Aramchol, ELA and PBI-4050, ELA and MSDC-0602k, ELA and VK-2809, ELA and MGL-3196, ELA and Vismodegib, ELA and CF-102 (Namodenoson), ELA and MT-3995 (Aparanerone), ELA and JKB-121 (Nalmefene), ELA and Emricasan, ELA and KD-025, and ELA and DUR-928.

In a further particular variant of this embodiment, component (ii) is not OCA or CVC.

In a particular embodiment, component (i) is Elafibranor or a pharmaceutically acceptable salt thereof, and component (ii) is selected from an ACC inhibitor, an ASK1 inhibitor, a dual NOX1 and NOX4, a VAP-1 inhibitor, a stearoyl CoA desaturase-1 inhibitors/fatty acid bile acid conjugate, a GPR84 antagonist/FFAR1 agonist or immunomodulator, a mTOR modulator or insulin sensitizer, a THRβ agonist, a hedgehog signaling pathway inhibitor, an adenosine A3 receptor agonist, an aldosterone receptor antagonist, a TLR-4 antagonist, a caspase inhibitor, a ROCK2 inhibitor, and a nuclear receptor ligand.

In a particular embodiment, component (i) is Elafibranor or a pharmaceutically acceptable salt thereof, and component (ii) is an ACC inhibitor (in particular GS-0976 or CP-640186 or Gemcabene), an ASK1 inhibitor (in particular Selonsertib), a dual NOX1 and NOX4 inhibitor (in particular GKT-831, formerly GKT137831), a VAP-1 inhibitor (in particular BI-1467335/PXS-4728A), a stearoyl CoA desaturase-1 inhibitors/fatty acid bile acid conjugate (in particular Aramchol), a GPR84 antagonist/FFAR1 agonist or immunomodulator (in particular PBI-4050), a mTOR modulator or insulin sensitizer (in particular MSDC-0602k), a THRb agonist (in particular VK-2809 or MGL-3196), a hedgehog signaling pathway inhibitor (in particular Vismodegib), an adenosine A3 receptor agonist (in particular CF-102 (Namodenoson)), an aldosterone receptor antagonist (in particular MT-3995 (Aparanerone)), a TLR-4 antagonist (in particular JKB-121 (Nalmefene)), a caspase inhibitor (in particular emricasan), a ROCK2 inhibitor (in particular KD-025), and a nuclear receptor ligand (in particular DUR-928).

In a particular embodiment, component (i) is Elafibranor or a pharmaceutically acceptable salt thereof, and component (ii) is an ASK1 inhibitor, a dual NOX1 and NOX4, a VAP-1 inhibitor, a stearoyl CoA desaturase-1 inhibitors/fatty acid bile acid conjugate, a GPR84 antagonist/FFAR1 agonist or immunomodulator, a mTOR modulator or insulin sensitizer, a THR3 agonist, a hedgehog signaling pathway inhibitor, an adenosine A3 receptor agonist, an aldosterone receptor antagonist, a TLR-4 antagonist, a caspase inhibitor, a ROCK2 inhibitor, and a nuclear receptor ligand.

In a particular embodiment, component (i) is Elafibranor or a pharmaceutically acceptable salt thereof, and component (ii) is an ASK1 inhibitor (in particular Selonsertib), a dual NOX1 and NOX4 inhibitor (in particular GKT-831, formerly GKT137831), a VAP-1 inhibitor (in particular BI-1467335/PXS-4728A), a stearoyl CoA desaturase-1 inhibitors/fatty acid bile acid conjugate (in particular Aramchol), a GPR84 antagonist/FFAR1 agonist or immunomodulator (in particular PBI-4050), a mTOR modulator or insulin sensitizer (in particular MSDC-0602k), a THRb agonist (in particular VK-2809 or MGL-3196), a hedgehog signaling pathway inhibitor (in particular Vismodegib), an adenosine A3 receptor agonist (in particular CF-102 (Namodenoson)), an aldosterone receptor antagonist (in particular MT-3995 (Apararenone)), a TLR-4 antagonist (in particular JKB-121 (Nalmefene)), a caspase inhibitor (in particular emricasan), a ROCK2 inhibitor (in particular KD-025), and a nuclear receptor ligand (in particular DUR-928).

In a particular embodiment, component (i) is Elafibranor or a pharmaceutically acceptable salt thereof, and component (ii) is an ACC inhibitor.

In a more particular embodiment, component (i) is Elafibranor or a pharmaceutically acceptable salt thereof, and component (ii) is GS-0976, CP-640186 or Gemcabene.

In a more particular embodiment, component (i) is Elafibranor or a pharmaceutically acceptable salt thereof, and component (ii) is GS-0976.

In a more particular embodiment, component (i) is Elafibranor or a pharmaceutically acceptable salt thereof, and component (ii) is CP-640186.

In a more particular embodiment, component (i) is Elafibranor or a pharmaceutically acceptable salt thereof, and component (ii) is Gemcabene.

In a particular embodiment, component (i) is Elafibranor or a pharmaceutically acceptable salt thereof, and component (ii) is an ASK1 inhibitor.

In a more particular embodiment, component (i) is Elafibranor or a pharmaceutically acceptable salt thereof, and component (ii) is Selonsertib.

In a particular embodiment, component (i) is Elafibranor or a pharmaceutically acceptable salt thereof, and component (ii) is a dual NOX1 and NOX4 inhibitor.

In a more particular embodiment, component (i) is Elafibranor or a pharmaceutically acceptable salt thereof, and component (ii) is GKT-831.

In a particular embodiment, component (i) is Elafibranor or a pharmaceutically acceptable salt thereof, and component (ii) is a VAP-1 inhibitor.

In a more particular embodiment, component (i) is Elafibranor or a pharmaceutically acceptable salt thereof, and component (ii) is BI-1467335/PXS-4728A.

In a particular embodiment, component (i) is Elafibranor or a pharmaceutically acceptable salt thereof, and component (ii) is a stearoyl CoA desaturase-1 inhibitors/fatty acid bile acid conjugate.

In a more particular embodiment, component (i) is Elafibranor or a pharmaceutically acceptable salt thereof, and component (ii) is Aramchol.

In a particular embodiment, component (i) is Elafibranor or a pharmaceutically acceptable salt thereof, and component (ii) is a GPR84 antagonist/FFAR1 agonist.

In a more particular embodiment, component (i) is Elafibranor or a pharmaceutically acceptable salt thereof, and component (ii) is PBI-4050.

In a particular embodiment, component (i) is Elafibranor or a pharmaceutically acceptable salt thereof, and component (ii) is a mTOR modulator or insulin sensitizer.

In a more particular embodiment, component (i) is Elafibranor or a pharmaceutically acceptable salt thereof, and component (ii) is in particular MSDC-0602k.

In a particular embodiment, component (i) is Elafibranor or a pharmaceutically acceptable salt thereof, and component (ii) is a THRβ agonist.

In a more particular embodiment, component (i) is Elafibranor or a pharmaceutically acceptable salt thereof, and component (ii) is VK-2809 or MGL-3196.

In a more particular embodiment, component (i) is Elafibranor or a pharmaceutically acceptable salt thereof, and component (ii) is VK-2809.

In a more particular embodiment, component (i) is Elafibranor or a pharmaceutically acceptable salt thereof, and component (ii) is MGL-3196.

In a particular embodiment, component (i) is Elafibranor or a pharmaceutically acceptable salt thereof, and component (ii) is a Hedgehog cell signaling pathway inhibitor.

In a more particular embodiment, component (i) is Elafibranor or a pharmaceutically acceptable salt thereof, and component (ii) is Vismodegib.

In a particular embodiment, component (i) is Elafibranor or a pharmaceutically acceptable salt thereof, and component (ii) is an Adenosine A3 receptor agonist.

In a more particular embodiment, component (i) is Elafibranor or a pharmaceutically acceptable salt thereof, and component (ii) is CF-102 (Namodenoson).

In a particular embodiment, component (i) is Elafibranor or a pharmaceutically acceptable salt thereof, and component (ii) is an aldosterone receptor antagonist.

In a more particular embodiment, component (i) is Elafibranor or a pharmaceutically acceptable salt thereof, and component (ii) is MT-3995 (Apararenone).

In a particular embodiment, component (i) is Elafibranor or a pharmaceutically acceptable salt thereof, and component (ii) is a TLR-4 antagonist.

In a more particular embodiment, component (i) is Elafibranor or a pharmaceutically acceptable salt thereof, and component (ii) is JKB-121 (Nalmefene).

In a particular embodiment, component (i) is Elafibranor or a pharmaceutically acceptable salt thereof, and component (ii) is a nuclear receptor ligand.

In a more particular embodiment, component (i) is Elafibranor or a pharmaceutically acceptable salt thereof, and component (ii) is Emricasan.

In a particular embodiment, component (i) is Elafibranor or a pharmaceutically acceptable salt thereof, and component (ii) is a ROCK2 inhibitor.

In a more particular embodiment, component (i) is Elafibranor or a pharmaceutically acceptable salt thereof, and component (ii) is KD-025.

In a particular embodiment, component (i) is Elafibranor or a pharmaceutically acceptable salt thereof, and component (ii) is nuclear receptor ligand.

In a particular embodiment, component (i) is Elafibranor or a pharmaceutically acceptable salt thereof, and component (ii) is DUR-928.

In a particular embodiment, the combination product of the invention further comprises at least one other therapeutically active agent selected from JAK/STAT inhibitors and other anti-inflammatory agent and/or an immunosuppressant agent.

Illustrative anti-inflammatory and/or immunosuppressant agents comprise glucocorticoids, NSAIDS, cyclophosphamide, nitrosoureas, folic acid analogs, purine analogs, pyrimidine analogs, methotrexate, azathioprine, mercaptopurine, ciclosporin, myriocin, tacrolimus, sirolimus, mycophenolic acid derivatives, fingolimod and other sphingosine-1-phosphate receptor modulators, monoclonal and/or polyclonal antibodies against such targets as proinflammatory cytokines and proinflammatory cytokine receptors, T-cell receptor and integrins.

In another particular embodiment the combination of the invention may further comprise at least one therapeutically active agent with known antifibrotic activity such as pirfenidone or receptor tyrosine kinase inhibitors (RTKIs) such as Nintedanib, Sorafenib and other RTKIs, or angiotensin II (AT1) receptor blockers, or CTGF inhibitor, or any antifibrotic compound susceptible to interfere with the TGFβ and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ signaling.

In a specific embodiment of the invention, the other therapeutically active agent is a PPAR agonist.

In another particular embodiment, the PPAR agonist is a PPAR-alpha agonist, a PPAR-gamma agonist, a PPAR-delta agonist, a PPAR-alpha/gamma dual agonist, a PPAR alpha/delta dual agonist, a PPAR gamma/delta dual agonist or a PPAR alpha/gamma/delta pan agonist.

In a particular embodiment, the other therapeutically active agent is:
  at least one PPAR-alpha agonist;
  at least one PPAR-gamma agonist;
  at least one PPAR-delta agonist;
  at least one PPAR-alpha/delta dual agonist;
  at least one PPAR-alpha agonist and at least one PPAR delta agonist;
  at least one PPAR-alpha/gamma dual agonist;
  at least one PPAR-alpha agonist and at least one PPAR gamma agonist;
  at least one PPAR-gamma/delta dual agonist;
  at least one PPAR-gamma agonist and at least one PPAR delta agonist;
  at least one PPAR-alpha/gamma/delta pan agonist; and
  at least one PPAR-alpha agonist, at least one PPAR-gamma agonist and at least one PPAR-delta agonist.

In a particular embodiment, the combination product of the invention is a composition comprising components (i) and (ii) as described above, and a pharmaceutically acceptable carrier.

In a particular embodiment, the combination product is a kit of parts comprising components (i) and (ii) as described above, for sequential, separate or simultaneous use.

In a further embodiment, components (i) and (ii) are formulated in an injectable suspension, a gel, an oil, a pill, a tablet, a suppository, a powder, a capsule, an aerosol, an ointment, a cream, a patch, or means of galenic forms for a prolonged and/or slow release.

The present invention also relates to the combination product according to the invention, for use as a medicament.

The invention also relates to the combination product herein disclosed, for use in a method for the treatment of a disease. In another embodiment, the invention relates to a method for the treatment of a disease, comprising administering to a subject in need thereof a therapeutically effective amount of the combination product herein discloses. In another embodiment, it is provided the use of a combination product according to the invention, for the manufacture of a medicament for the treatment of a disease.

In particular, the combination product of the present invention is useful for the treatment of diseases such as immune, inflammatory, metabolic, fibrotic and cholestatic diseases. In a particular embodiment, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, keloid, old myocardial infarction, scleroderma/systemic sclerosis, inflammatory diseases, neurodegenerative diseases, cancers, liver cancer, hepatocellular carcinoma, gastrointestinal cancer, gastric cancer, meningioma associated with neurofibromatosis, pancreatic neuroendocrine tumors, pancreatic exocrine tumors, leukemia, myeloproliferative/myelodisplastic diseases, mastocytosis, dermatofibrosarcoma, solid tumors including breast, lung, thyroid or colorectal cancer, a prostate cancer, liver fibrosis or cirrhosis of any origin, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, skin fibrosis, epidermis fibrosis, endodermis fibrosis, skin fibrosis due to scleroderma/systemic sclerosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF), heart fibrosis, kidney fibrosis, nephrogenic systemic fibrosis, muscle fibrosis, soft tissue (e.g. mediastinum or retroperitoneum) fibrosis, bone marrow fibrosis, joint fibrosis, tendon fibrosis, cartilage fibrosis, pancreas fibrosis, uterus fibrosis, nervous system fibrosis, testis fibrosis, ovary fibrosis, adrenal gland fibrosis, artery fibrosis, vein fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, peri-implantational fibrosis and asbestosis, arthrofibrosis, adhesive capsulitis.

In a most preferred embodiment, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, liver cancer, hepatocallular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF).

In a further aspect, the invention relates to the combination of the invention, for use in the inhibition of proliferation and/or activation of fibroblasts responsible for the production of collagen fibers and/or responsible for the production of the extracellular matrix.

According to the present invention, the term "autoimmune diseases" is used to designate a condition that arises from an abnormal immune response of the body against substances and tissues normally present in the body. The disease may be restricted to certain organs (e.g. in type I diabetes or autoimmune thyroiditis) or involve a particular tissue in different places (e.g. in Goodpasture's disease, affection of the basement membrane in the lung and the kidney).

The term "inflammation" is used to designate a condition that arise from a protective response involving host cells, blood vessels, and proteins and other mediators which may serve to eliminate the cause of cell/tissue injury, as well as the necrotic cells/tissues resulting from the original insult, and to initiate the process of repair. The inflammatory reaction may be manifested by pain, heat, redness, swelling, blood vessels dilatation, blood flow increase and loss of function.

According to the present invention, the terms "fibrosis", "fibrotic disease", "fibrotic disorder" and declinations thereof denote a pathological condition of excessive deposition of fibrous connective tissue in an organ or tissue. More specifically, fibrosis is a pathological process, which includes a persistent fibrotic scar formation and overproduction of extracellular matrix by the connective tissue, as a response to tissue damage. Physiologically, the deposit of connective tissue can obliterate the architecture and function of the underlying organ or tissue.

According to the present invention, the fibrosis or fibrotic disorder may be associated with any organ or tissue fibrosis. Illustrative, non-limiting examples of particular organ fibrosis include liver, gut, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, soft tissue (e.g. mediastinum or retroperitoneum), bone marrow, joint or stomach fibrosis, in particular liver, kidney, skin, epidermis, endodermis, muscle, tendon, cartilage, heart, pancreas, lung, uterus, nervous system, testis, ovary, adrenal gland, artery, vein, colon, intestine (e.g. small intestine), biliary tract, soft tissue (e.g. mediastinum or retroperitoneum), bone marrow, joint, eye or stomach fibrosis.

According to the present invention, the terms "cholestasis" or "cholestatic disease", or "cholestatic disorder" and declinations thereof denote a pathological condition defined by a decrease in bile flow due to impaired secretion by hepatocytes or to obstruction of bile flow through intra- or extrahepatic bile ducts. Therefore, the clinical definition of cholestasis is any condition in which substances normally excreted into bile are retained.

In a particular embodiment, the fibrotic disorder is selected in the group consisting of a liver, gut, lung, heart, kidney, muscle, skin, soft tissue (e.g. mediastinum or retroperitoneum), bone marrow, intestinal, and joint (e.g. knee, shoulder or other joints) fibrosis.

In a preferred embodiment, the fibrotic disorder is selected in the group consisting of liver, lung, skin, kidney and intestinal fibrosis.

In a more preferred embodiment of the present invention, treated fibrotic disorder is selected in the group consisting of the following non exhaustive list of fibrotic disorders: non-alcoholic steatohepatitis (NASH), pulmonary fibrosis, idiopathic pulmonary fibrosis, skin fibrosis, eye fibrosis (such as capsular fibrosis), endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, lung fibrosis consecutive to chronic inflammatory airway disease (COPD, asthma, emphysema, smoker's lung, tuberculosis), alcohol or drug-induced liver fibrosis, liver cirrhosis, infection-induced liver fibrosis, radiation or chemotherapeutic-induced fibrosis, nephrogenic systemic fibrosis, Crohn's disease, ulcerative colitis, keloid, old myocardial infarction, scleroderma/systemic sclerosis, arthrofibrosis, some forms of adhesive capsulitis, chronic fibrosing cholangiopathies such as Primary Sclerosing Cholangitis (PSC) and Primary Biliary Cholangitis (PBC), biliary atresia, progressive familial intrahepatic cholestasis type 3 (PFIC3), peri-implantational fibrosis and asbestosis.

Cholestasis is defined as a decrease in bile flow due to impaired secretion by hepatocytes (hepato-cellular cholestasis) or to obstruction of bile flow through intra- or extrahepatic bile ducts (obstructive cholestasis). In clinical practice, cholestasis is any condition in which the flow of bile from the liver is slowed or blocked. According to a particular embodiment of the invention, the cholestestatic disease is selected in the group consisting of primary biliary cholangitis (PBC), primary sclerosing cholangitis (PSC), Intrahepatic Cholestasis of Pregnancy, Progressive Familial Intrahepatic Cholestasis, Biliary atresia, Cholelithiasis, Infectious Cholangitis, Cholangitis associated with Langerhans cell histiocytosis, Alagille syndrome, Nonsyndromic ductal paucity, Drug-induced cholestasis, and Total parenteral nutrition-associated cholestasis. In a preferred embodiment, the cholestatic disease is PBC or PSC, in particular PBC.

Examples of inflammatory diseases, fibrotic diseases, metabolic diseases and cholestatic diseases include metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, keloid, old myocardial infarction, scleroderma/systemic sclerosis, inflammatory diseases, neurodegenerative diseases, cancers, liver cancer, hepatocallular carcinoma, gastrointestinal cancer, gastric cancer, meningioma associated with neurofibromatosis, pancreatic neuroendocrine tumors, pancreatic exocrine tumors, leukemia, myeloproliferative/myelodisplastic diseases, mastocytosis, dermatofibrosarcoma, solid tumors including breast, lung, thyroid or colorectal cancer, a prostate cancer, liver fibrosis or cirrhosis of any origin, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, skin fibrosis, epidermis fibrosis, endodermis fibrosis, skin fibrosis due to scleroderma/systemic sclerosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF), heart fibrosis, kidney fibrosis, nephrogenic systemic fibrosis, muscle fibrosis, soft tissue (e.g. mediastinum or retroperitoneum) fibrosis, bone marrow fibrosis, joint fibrosis, tendon fibrosis, cartilage fibrosis, pancreas fibrosis, uterus fibrosis, nervous system fibrosis, testis fibrosis, ovary fibrosis, adrenal gland fibrosis, artery fibrosis, vein fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, peri-implantational fibrosis and asbestosis, arthrofibrosis, adhesive capsulitis.

Preferably, the disease is selected in the group consisting of metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies such as Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, liver cancer, hepatocallular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, intestine (e.g. small intestine) fibrosis, colon fibrosis, stomach fibrosis, lung fibrosis, lung fibrosis consecutive to chronic inflammatory airway diseases, such as COPD, asthma, emphysema, smoker's lung, tuberculosis, pulmonary fibrosis, idiopathic pulmonary fibrosis (IPF).

The term "treatment" or "treating" refers to the curative or preventive of a disorder in a subject in need thereof. The treatment involves the administration of the compound, in particular comprised in a pharmaceutical composition, to a subject having a declared disorder, i.e. to a patient, to cure, delay, reverse, or slow down the progression of the disorder, improving thereby the condition of the subject. A treatment may also be administered to a subject that is healthy or at risk of developing a cholestatic or fibrotic disorder to prevent or delay the disorder.

Therefore, according to the invention, the treatment of an immune, inflammatory, metabolic, fibrotic and cholestatic disease involves the administration of the combination of the present invention, for example in the form of a pharmaceutical composition containing components (i) and (ii) of the combination, to a subject having a declared disorder to cure, delay, reverse or slow down the progression of the disorder, thus improving the condition of the patient or to a healthy subject, in particular a subject who is at risk of developing such disease.

The treatment involves the administration of the combination of the invention to a patient having a declared disorder to cure, delay, or slow down the progress, thus improving the condition of the patient or to a healthy subject, in particular a subject who is at risk of developing an inflammatory, metabolic, fibrotic and cholestatic disease.

The subject to be treated is a mammal, preferably a human. The subject to be treated according to the invention can be selected on the basis of several criteria associated to fibrotic diseases such as previous drug treatments, associated pathologies, genotype, exposure to risk factors, viral infection, as well as on the basis of the detection of any relevant biomarker that can be evaluated by means of imaging methods and immunological, biochemical, enzymatic, chemical, or nucleic acid detection methods.

The subjects to be treated according to the invention can be selected on the basis of several criteria associated to inflammatory, metabolic, fibrotic and cholestatic diseases such as previous drug treatments, associated pathologies, genotype, exposure to risk factors, viral infection, as well as any other relevant biomarker that can be evaluated by means of imaging methods and immunological, biochemical, enzymatic, chemical, or nucleic acid detection method.

In a particular embodiment, the treatment of an inflammatory, metabolic, fibrotic and cholestatic disease may comprise the administration of a composition comprising at least two compounds of formula (I). In this embodiment, the administered component (ii) is provided in the same composition as the at least two compounds of formula (I), or in a separate form, such as in a different composition.

In another embodiment, the combination of the invention is for simultaneous, sequential or separate administration in therapy, therefore being possibly included in different compositions. In case of sequential administration, the compound of formula (I), in particular ELA, may be administrated prior to component (ii), or component (ii) is (are) administrated prior to the compound of formula (I).

A compound of formula (I) may be formulated as pharmaceutically acceptable salts, particularly acid or base salts compatible with pharmaceutical use. Salts of compounds of formula (I) include pharmaceutically acceptable acid addition salts, pharmaceutically acceptable base addition salts, pharmaceutically acceptable metal salts, ammonium and alkylated ammonium salts. These salts can be obtained during the final purification step of the compound or by incorporating the salt into the previously purified compound.

The pharmaceutical compositions of the present invention can also comprise one or several excipients or vehicles, acceptable within a pharmaceutical context (e.g. saline solutions, physiological solutions, isotonic solutions, etc., compatible with pharmaceutical usage and well-known by one of ordinary skill in the art).

These compositions can also comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc.

These compositions can be formulated in the form of injectable suspensions, gels, oils, ointments, pills, tablets, suppositories, powders, gel caps, capsules, aerosols, etc., eventually by means of galenic forms or devices assuring a prolonged and/or slow release. For this kind of formulation, agents such as cellulose, carbonates or starches can be advantageously used.

The pharmaceutical compositions of the present invention comprising a compound of formula (I) and one or more component(s) (ii) may be administered by different routes and in different forms. For example, the compound(s) may be administered via a systemic way, per os, parenterally, by inhalation, by nasal spray, by nasal instillation, or by injection, such as for example intravenously, by intra-muscular route, by subcutaneous route, by transdermal route, by topical route, by intra-arterial route, etc.

Of course, the route of administration will be adapted to the form of the compounds to be administered, according to procedures well known by those skilled in the art.

Components (i) and (ii) of the combination product of the invention are administered in a therapeutically effective amount. Within the context of the invention, the term "effective amount" refers to an amount of the compound sufficient to produce the desired therapeutic result.

The frequency and/or dose relative to the administration can be adapted by one of ordinary skill in the art, in function of the patient, the pathology, the form of administration, etc. Typically, the combination (such as in the form of a pharmaceutical composition or a kit-of-parts) of the present invention can be administered for the treatment of a fibrotic disease at a dose for component (i) or component (ii), comprised between 0.01 mg/day to 4000 mg/day, such as from 50 mg/day to 2000 mg/day, and particularly from 100 mg/day to 1000 mg/day.

In a preferred embodiment of the invention, ELA is used in combination with component (ii) at a dose comprised between 80 to 120 mg/day for Elafibranor.

In another preferred embodiment, the active ingredients are administered as one or more pharmaceutical composition(s) in the form of a pill or tablet intended for an oral ingestion.

Administration can be performed daily or even several times per day, if necessary.

The invention is further described with reference to the following, non-limiting, examples.

DESCRIPTION OF THE FIGURES

Abbreviations used in the figures, in the tables, and in the text:
α-SMA α-Smooth Muscle Actin
AP-1 Activator Protein 1
ASBTi Apical Sodium-codependent Bile acid Transporter inhibitor
ASK1 Apoptosis Signal-regulating Kinase 1
AT1 Angiotensin II receptor type 1
CLA Conjugated Linoleic Acid
COPD Chronic Obstructive Pulmonary Disease
CTGF Connective Tissue Growth Factor
CVC Cenicriviroc
DGAT DiacylGlycerol-O-AcylTransferase
DMSO DiMethyl SulfOxide
DPP4 DiPeptidyl Peptidase 4
ELISA Enzyme-Linked Immuno Assay
EOB Excess Over Bliss
EOBHSA Excess Over Bliss Highest Single Agent
FABAC Fatty Acid Bile Acid Conjugate
FBS Fetal Bovine Serum
FGF Fibroblast Growth Factor
FXR Farnesoid X Receptor
GDF Growth Differentiation Factor
GLP-1 Glucagon-Like Peptide-1
GPCR G-Protein Coupled Receptor
HBV Hepatitis B Virus
HCV Hepatitis C Virus
15-HEPE 5-HydroxyEicosaPentaEnoic acid
HIV Human Immunodeficiency Virus
HSC Hepatic Stellate Cell
IC50 half maximal Inhibitory Concentration
iNOS inducible Nitric Oxide Synthase
IPF Idiopathic Pulmonary Fibrosis
LO LipOxygenase
LPS LipoPolySaccharide
LT LeukoTriene
MAPK Mitogen-Activated Protein Kinase
MMP-9 Matrix Metalloproteinase 9
MMPase Matrix Metalloproteinase
NADPH Nicotinamide Adenine Dinucleotide PHosphate
NAFLD Non-Alcoholic Fatty Liver Disease
NASH Non-Alcoholic SteatoHepatitis
NF-κB Nuclear Factor-kappa B
NOX NADPH oxidase
NSAIDs Non-Steroid Anti-Inflammatory Drugs
PAR Protease-Activated Receptor
PBC Primary Biliary Cholangitis
PBS Phosphate-Buffered Saline PDE PhosphoDiEsterase
PDGF Platelet-Derived Growth Factor
PFIC3 Progressive Familial Intrahepatic Cholestasis type 3
PFOR Pyruvate: Ferredoxin OxidoReductase
PPAR Peroxisome Proliferator Activated-Receptor
PPRE PPAR Response Elements
PSC Primary Sclerosing Cholangitis
ROCK Rho-associated protein kinase
RTK Receptor Tyrosine Kinase
SGLT Sodium-GLucose transport
STAT Signal Transducers and Activators of Transcription
TGFβ Transforming Growth Factor β
TGFBRI TGFβ receptors type I
TGFBRII TGFβ receptors type II
THBS1 Thrombospondin 1
THR β Thyroid Hormone Receptor β
TIMP Tissue Inhibitor of MetalloProteinase 1
TLR-4 Toll Like Receptor 4
VAP-1 Vascular Adhesion Protein-1
VDR Vitamin D Receptor

Serum-deprived HSC were preincubated for 1 hour with Elafibranor (A), Cenicriviroc (B), or Bezafibrate (PPAR pan α/γ/δ) before the activation with the profibrogenic cytokine TGFβ1 (1 ng/ml).

After 48 hours of incubation, the expression of α-SMA was measured by ELISA.

The obtained values were transformed into percentage inhibition over TGFβ1 control. Data are presented as mean (triplicates)±standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 1 ng/mL group)]. The curve fitting and the calculation of half maximal inhibitory concentration ($IC_{50}$) were performed with XLFit software 5.3.1.3.

Figure 7:
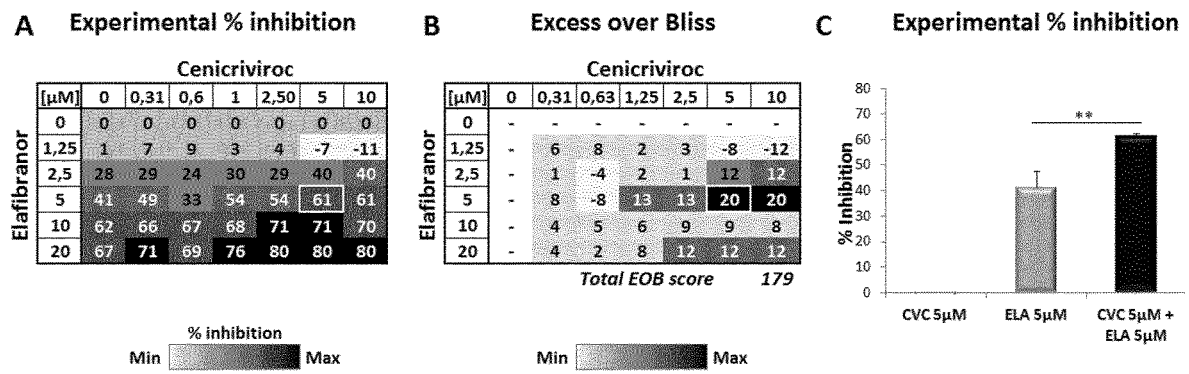

FIG. 7: Combination of Elafibranor with Cenicriviroc synergistically inhibits α-SMA in TGFβ1-induced hHSC.

Combinations were tested in a dose-response matrix format and analyzed according to the excess over Bliss (EOB) additivism model.

Dilution series of Elafibranor (row) and Cenicriviroc (column) were prepared, including their respective DMSO controls.

The resulting mixes were added to serum-deprived HSC, 1 hour prior to the activation with the profibrogenic cytokine TGFβ1 (1 ng/ml).

(A) Percentage of α-SMA inhibition over the TGFβ1 control for all combination pairs. Data are presented as mean of quadruplicates.

(B) EOB scores were calculated as described in Materials and Methods. Any compound pair with EOB values>10 was considered synergistic (colored from light grey to black). The total EOB score including all combinations was also calculated.

(C) Data values derived from a synergistic combination pair were plotted in a bar graph representation. Data are presented as mean (quadruplicates)±standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus 'product combination' group)].

Figure 8:
Figure 8:

FIG. 8: Bezafibrate does not synergize with Cenicriviroc to reduce fibrosis in TGFβ1-induced hHSC.

Combinations were tested in a dose-response matrix format and analyzed according to the excess over Bliss additivism model.

Dilution series of Bezafibrate (row) and Cenicriviroc (column) were prepared, including their respective DMSO controls. The resulting mixes were added to serum-deprived HSC, 1 hour prior to the activation with the profibrogenic cytokine TGFβ1 (1 ng/ml).

(A) Percentage inhibition of α-SMA over the TGFβ1 control.

(B) Excess over Bliss (EOB) scores were calculated as described in Materials and Methods. Any compound pair with EOB values>10 was considered synergistic (colored from light grey to black). The total EOB score including all combinations was also calculated.

Figure 9:
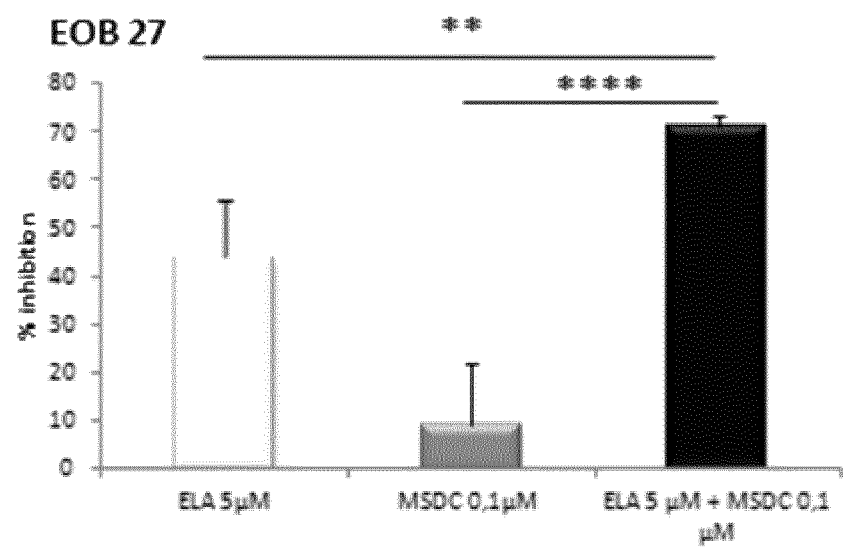
Figure 9:
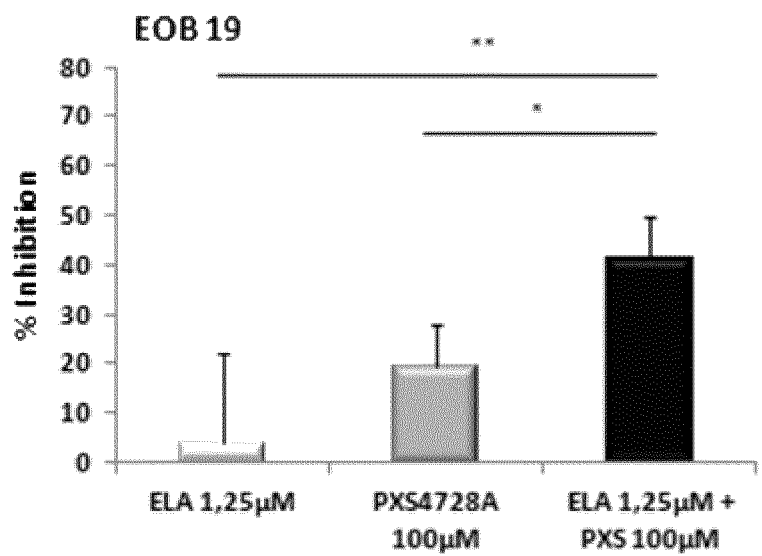
Figure 9:
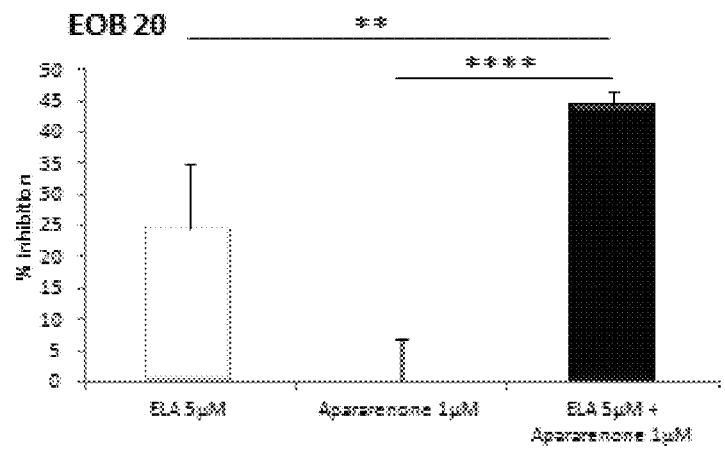
Figure 9:
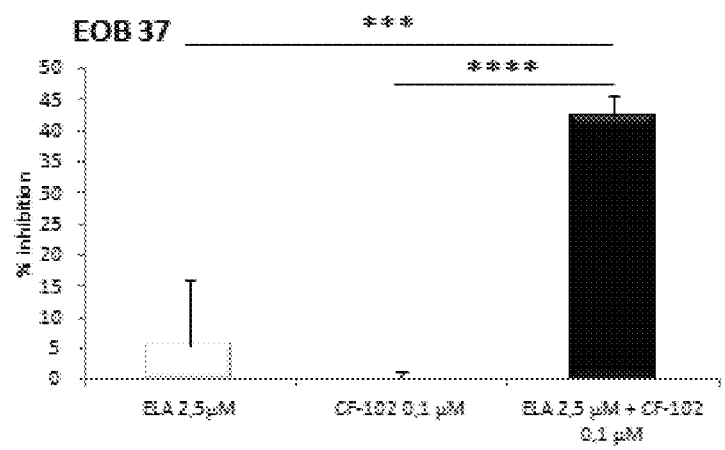
Figure 9:
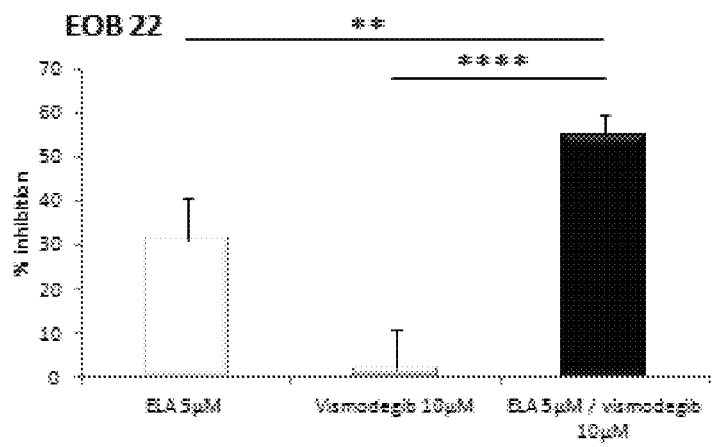
Figure 9:
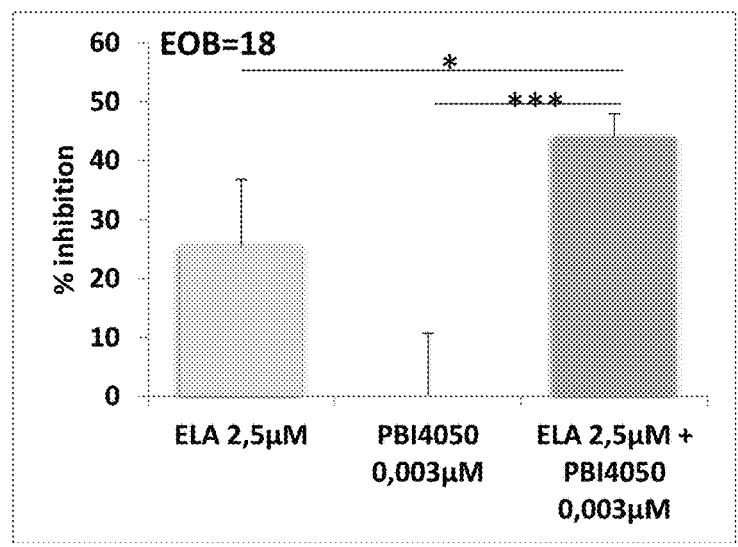
Figure 9:
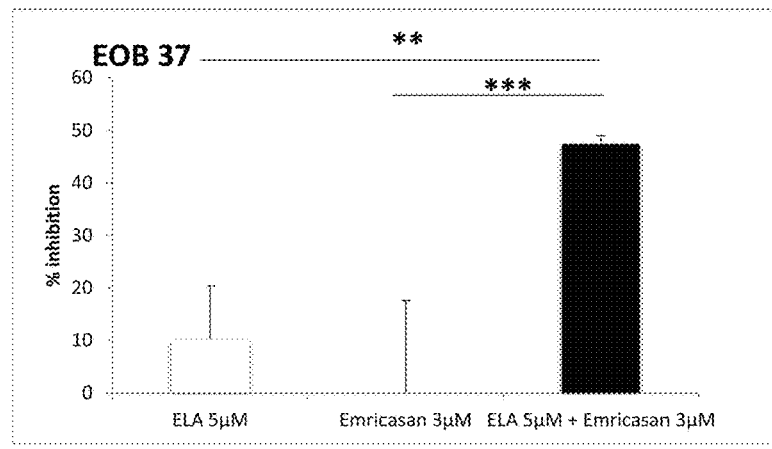
Figure 9:
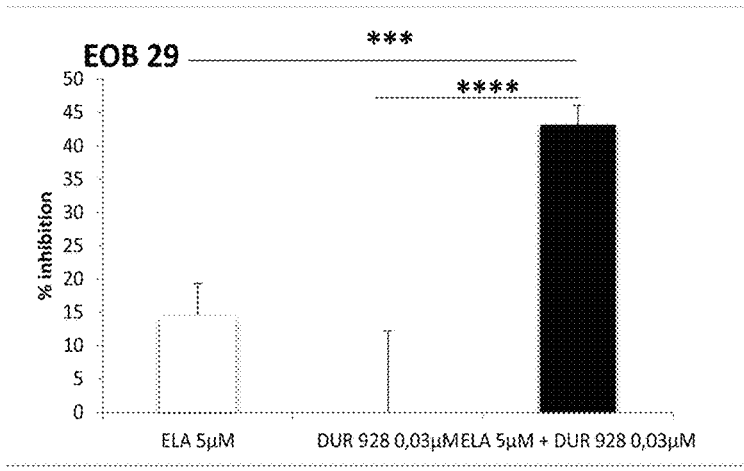

FIG. 9: Combinations of elafibranor with MSDC-0602, PXS-4728A, Apararenone, CF-102, Vismodegib, PBI-4050, KD-025, DUR-928, VK-2809, and Emricasan synergistically inhibit α-SMA in TGFβ1-induced hHSC.

Combinations were tested in a dose-response matrix format and analyzed according to the Excess Over Bliss (EOB) additivism model. Percentages of α-SMA inhibition over the TGFβ1 control were plotted in a bar graph representation for representative synergistic combinations. Data are presented as mean (quadruplicates)±standard deviation (SD). *: $p<0.05$; : $p<0.01$; *: $p<0.001$ using One-way ANOVA and Fisher's Least Significant Difference (LSD) post-hoc test. MSDC=MSDC-0602.

Figure 10:
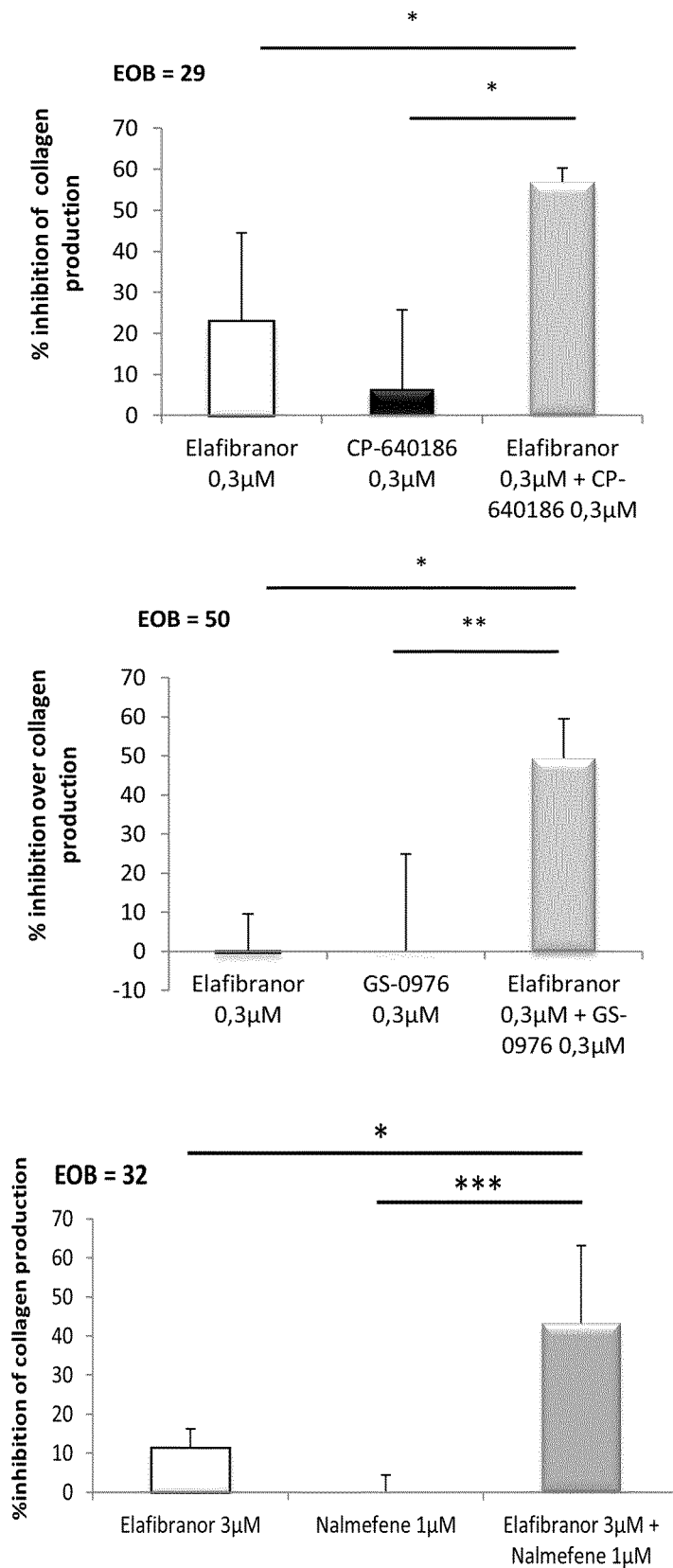

FIG. 10: Combinations of elafibranor with CP-640186, GS-0976 or JKB-121 (Nalmefene) synergistically inhibit collagen production in liver microtissues.

Microtissues were treated with a metabolic induction of NASH stimulus with or without elafibranor alone (white bar), compound (ii) alone (black bar) or a combination of both (grey bar). Combinations were tested in a dose-response matrix format and analyzed according to the Excess Over Bliss (EOB) additivism model. Percentages of inhibition over the NASH stimulus control were plotted in a bar graph representation for representative synergistic combinations. Data are presented as mean (triplicates)±standard deviation (SD). *: $p<0.05$; : $p<0.01$; *: $p<0.001$ using One-way ANOVA and Fisher's Least Significant Difference (LSD) post-hoc test.

Figure 11:
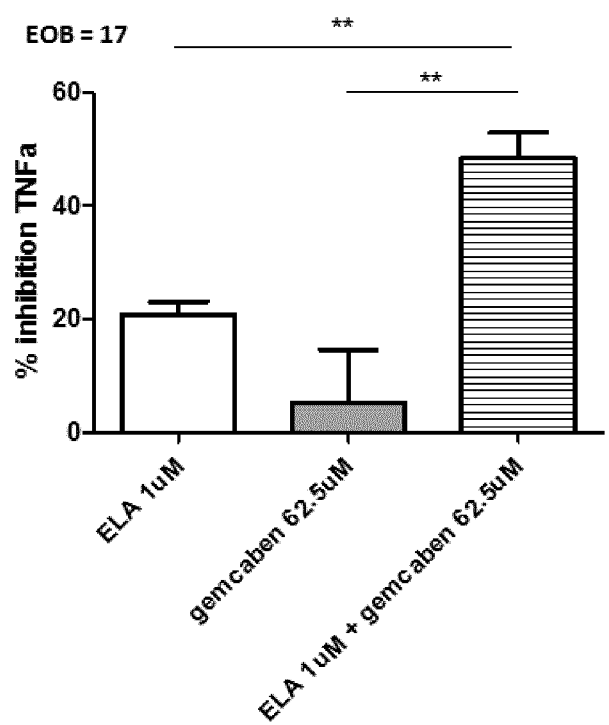

FIG. 11: Combination of elafibranor with gemcabene synergistically inhibits TNFα secretion in LPS-activated macrophages.

Combinations were tested in a dose-response matrix format and analyzed according to the Excess Over Bliss (EOB) additivism model. Percentages of inhibition of TNFα secretion over the LPS control were plotted in a bar graph representation for representative synergistic combinations. Data are presented as mean (quadruplicates)±standard deviation (SD). *: $p<0.05$; : $p<0.01$; *: $p<0.001$ using One-way ANOVA and Fisher's Least Significant Difference (LSD) post-hoc test.

Figure 12:
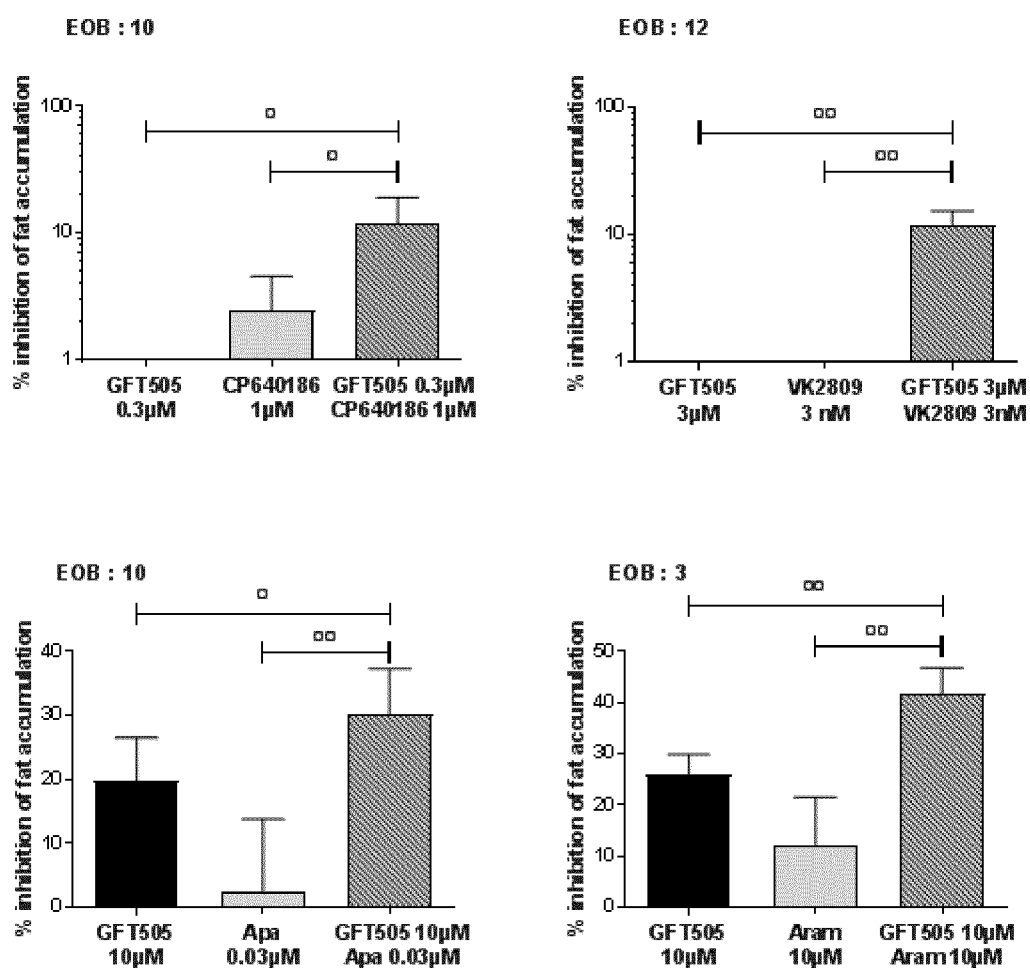

FIG. 12: Combinations of Elafibranor with CP640186, VK-2809, Apararenone (Apa) or Aramchol (Aram) synergistically inhibit fat accumulation in HepG2.

Combinations were tested in a dose-response matrix format and analyzed according to the Excess Over Bliss (EOB) additivism model. Percentages of inhibition of fat accumulation over the FFA-treated control were plotted in a bar graph representation for representative synergistic combinations. Data are presented as mean (quadruplicates)±standard deviation (SD). *: $p<0.05$; : $p<0.01$; *: $p<0.001$ using One-way ANOVA and Fisher's Least Significant Difference (LSD) post-hoc test.

Figure 13:
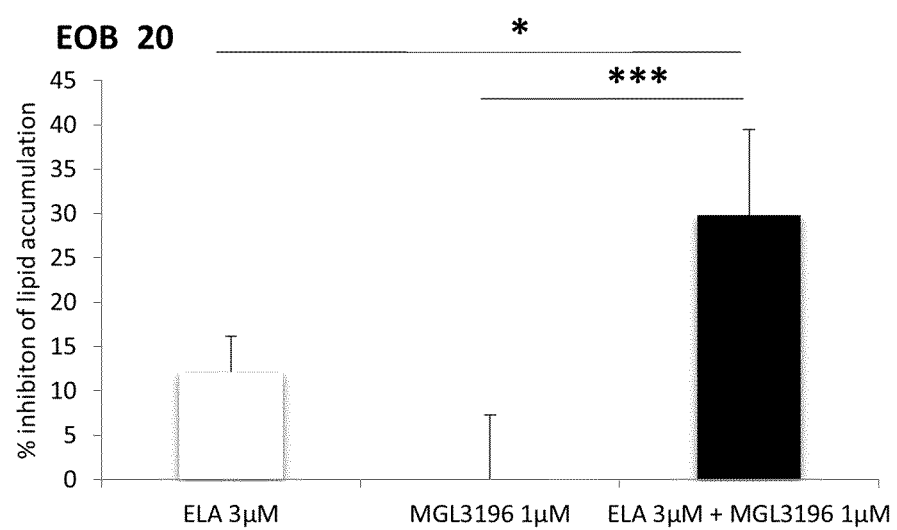

FIG. 13: Combination of elafibranor with MGL-3196 synergistically inhibits fat accumulation in 3D Huh7 spheroid culture.

Spheroids were treated with a metabolic NASH stimulus with or without elafibranor alone (white bar), MGL3196 alone (grey bar) or a combination of both (black bar). Measurement of lipid accumulation was performed as described in material and methods. Standard deviations are shown as error bars (n=3). Calculated EOB value is stated in the top left. Significant differences (*$p<0.05$; $p<0.01$*; $p<0.001$) following one-way analysis of variance (ANOVA) and Fisher's Least Significant Difference (LSD) test.

Figure 14:
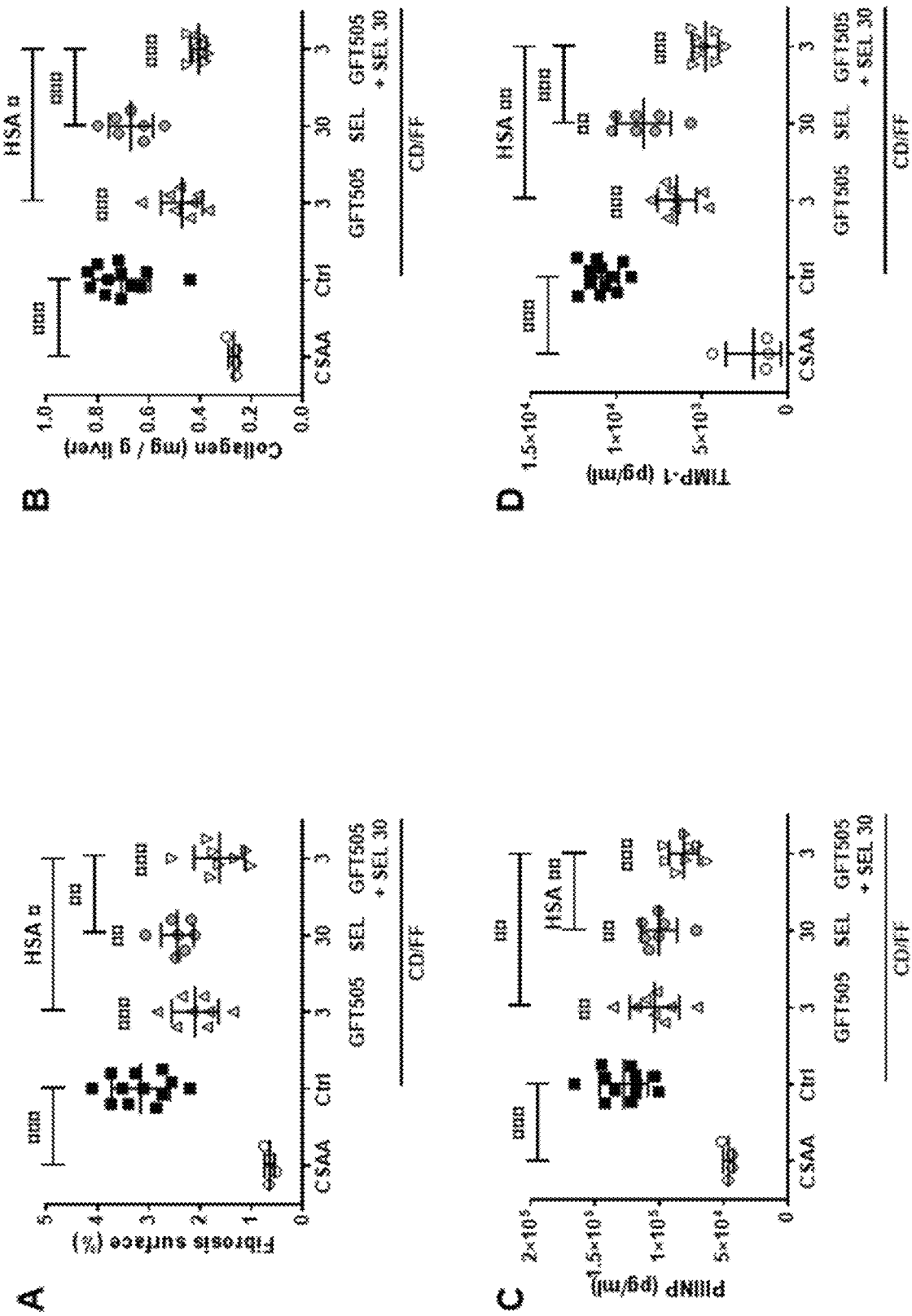
Figure 14:
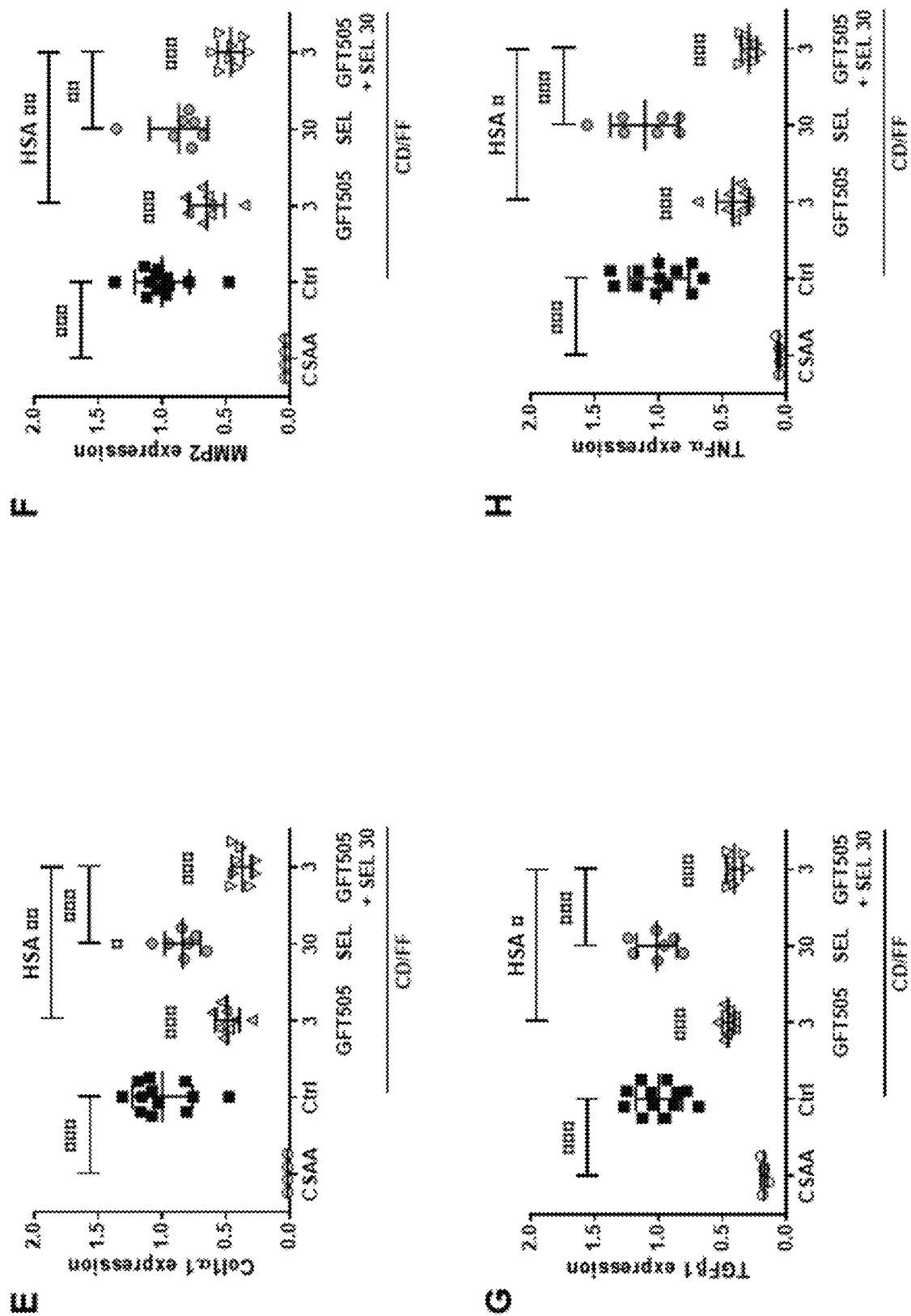

FIG. 14: Elafibranor (GFT505, 3 mg/kg/day) and selonsertib (SEL, 30 mg/kg/day) synergize to reduce fibrosis, tissue remodeling and inflammatory markers in mice with NASH (CDFF-fed mice).

(A) Percentage of fibrosis surface was assessed by morphometric quantification of picrosirius positive area relative to the liver section area.

(B) Hepatic collagen content.

(C) Plasma PIIINP concentration, surrogate markers of hepatic fibrosis.

(D) Plasma TIMP1 concentration, surrogate markers of hepatic fibrosis.

Expression of Col1α1 (E), MMP2 (F), TGFβ1 (G) as markers of fibrosis and tissue remodeling, and TNFα (H) and CCR2 (I), markers of inflammation, was assessed by real time quantitative PCR.

Data are expressed as mean±SD. ¤ $p<0.05$, ¤¤ $p<0.01$, ¤¤¤ $p<0.001$ using one-tailed Student t-test with Welsh correction. HSA, Highest Single Agent model.

Figure 15:
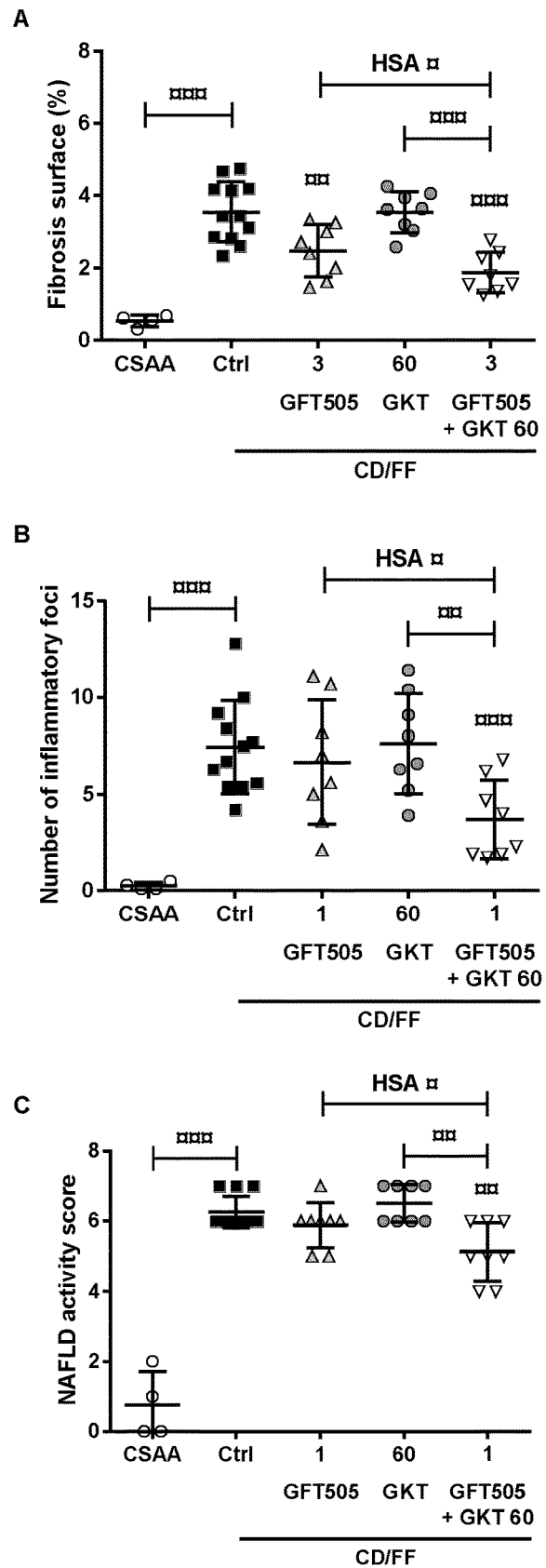

FIG. 15: Elafibranor (GFT505, 1 or 3 mg/kg/day) and GKT-831 (GKT, 60 mg/kg/day) synergize to reduce NASH and fibrosis in mice with NASH (CDFF-fed mice).

(A) Percentage of fibrosis surface was assessed by morphometric quantification of picrosirius positive area relative to the liver section area.

(B) Histological evaluation of inflammatory foci on 10 microscope field areas (20×).

(C) NAFLD activity score, assessed by the calculation of the sum of steatosis, ballooning and lobular inflammation grades (minimum 0-maximum 8) according to the NASH Clinical Research Network (Kleiner 2005, Brunt 1999).

Data are expressed as mean±SD. ¤ $p<0.05$, ¤¤ $p<0.01$, ¤¤¤ $p<0.001$ using one-tailed Student t-test with Welsh correction. $ $p<0.05$, $$ $p<0.01$, $$$ $p<0.001$ using one-tailed Mann-Whitney U (non-parametric) test. HSA, Highest Single Agent model.

Figure 16:
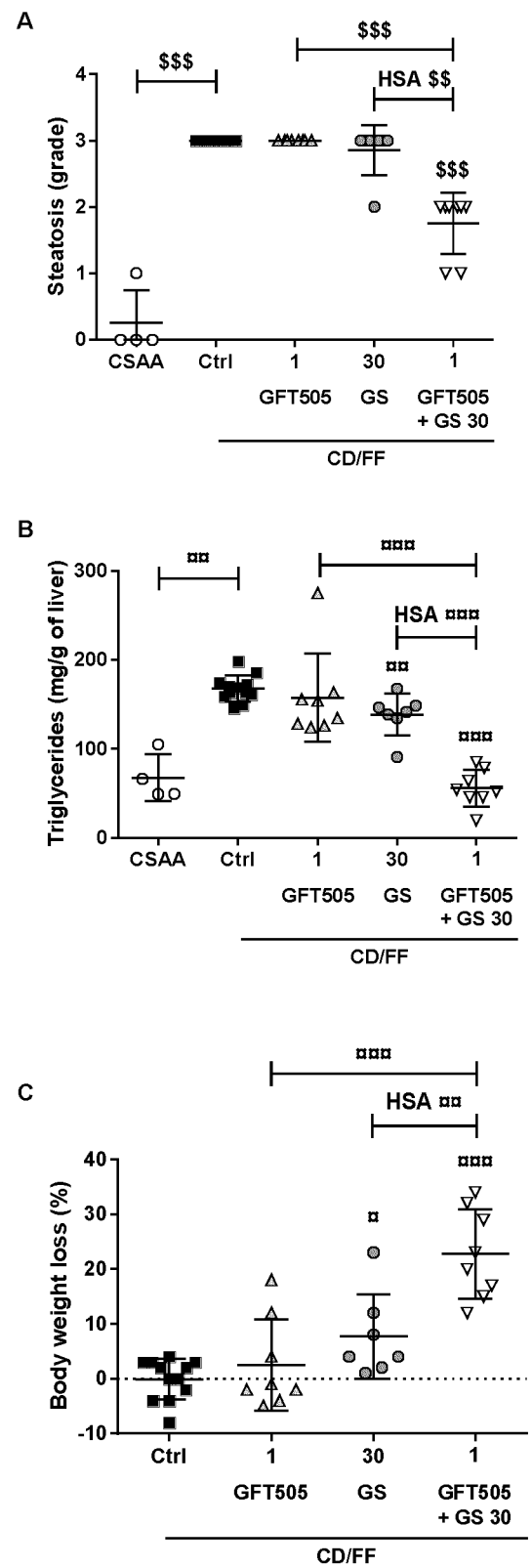

FIG. 16: Elafibranor (GFT505, 1 mg/kg/day) and GS-0976 (GS, 30 mg/kg/day) synergize to reduce steatosis and body weight in mice with NASH (CDFF-fed mice).

(A) Steatosis grade, assessed by histological examination according to the NASH Clinical Research Network guidelines.

(B) Hepatic triglyceride content.

(C) Body weight loss after 8 weeks of treatment compared to the controls.

Data are expressed as mean±SD. ¤ $p<0.05$, ¤¤ $p<0.01$, ¤¤¤ $p<0.001$ using one-tailed Student t-test with Welsh correction. HSA, Highest Single Agent model.

EXAMPLES

Example 1: Combination Therapy Study Design

Materials and Methods

Compounds were dissolved in dimethyl sulfoxide (DMSO, Fluka cat #41640).

1. Illustration in the Model of TGF β1-Induced hHSC hHSC Culture

The human primary hepaticstellate cells (hHSC) (Innoprot) were cultured in STeCM medium (ScienCell cat #5301) that was supplemented with 2% fetal bovine serum (FBS, ScienCell cat #0010), 1% penicillin/streptomycin (ScienCell cat #0503) and stellate cell growth supplement (SteCGS; ScienCell cat #5352). Cell culture flasks were coated with Poly-L Lysine (Sigma cat #P4707) for a better adherence.

Preparation of Compositions

2 Components Combination Matrix

For these experiments, a checkerboard matrix was generated. ELA and component (ii) stocks were serially diluted in DMSO in 5-points series in a row (ELA) and a 11-points series in a column (component (ii)) of a 96-well plate. Subsequently, the 5×11 combination matrix was generated by 1:1 mixing of all single agent concentrations. The test concentrations for each compound were chosen based on the respective $IC_{50}$ of each compound as single agent obtained by measuring α-SMA content in the HSC model stimulated with TGF-β1.

Activation of hHSC with TGF-β1 and Compound Treatment

The human primary hepatic stellate cells (hHSC) (Innoprot) were cultured under standard conditions, as described above. The cells were subsequently plated at a density of $2×10^4$ cells/well into 96-well plates for the measure of α-SMA by ELISA. The next day, cell-culture medium was removed, and cells were washed with PBS (Invitrogen cat #14190). hHSC were deprived for 24 hours in serum-free and SteCGS-free medium. For the treatments with ELA, component (ii) and the respective ELA/component (ii) combinations, the serum-deprived hHSC were preincubated for 1 hour with the compounds followed by addition of the profibrogenic stimuli TGF-β1 (PeproTech cat #100-21, 1 ng/mL) in serum-free and SteCGS-free medium for an additional 48 hour period.

α-SMA ELISA

The level of α-SMA was measured using a Sandwich ELISA. Briefly, the wells of an ELISA plate were first coated with the capture antibody (mouse monoclonal anti-ACTA2, Abnova) at 4° C. overnight. After 3 washes in PBS+0.2% Tween 20, a blocking solution consisting of PBS+0.2% BSA was added for one hour followed by another washing cycle. The cell lysates were transferred into the wells for binding to the capture antibody for a period of 2 h at room temperature. After the washing procedure, the detection antibody (biotinylated mouse monoclonal anti-ACTA2, Abnova) was added for 2 hours at room temperature followed by 3 washes. For the detection, an HRP-conjugated Streptavidin (R&D Systems cat #DY998) was first applied for 30 min at room temperature. After washing, the HRP substrate TMB (BD, #555214) was added and incubated for 7 min at room temperature in the dark. Upon oxidation, TMB forms a water-soluble blue reaction product that becomes yellow with addition of sulfuric acid (solution stop), enabling accurate measurement of the intensity at 450 nm using a spectrophotometer. The developed color is directly proportional to the amount of α-SMA present in the lysate.

2. Illustration in the Model of HSC Activation in 3D Human Liver Microtissue

3D Human Liver Microtissue Culture

Cryopreserved primary human hepatocytes (IPHH_11) and cryopreserved primary human non parenchymal cells (NPCs, IPHN_11) were obtained from BioreclamationIVT. The cryopreserved human primary hepatic stellate cells (hHSC) were obtained from Innoprot. 3D INSIGHT Human Liver Microtissues (MT-02-302-95; InSphero AG) were produced with the IPHH_11, the IPHN_11 and the hHSC in a 96-well hanging-drop culture platform (GravityPLUS). After microtissues formation, they were transferred into a microtissue-specific 96-well culture and assay platform (GravityTRAP). Further maintenance and compound treatments were performed in GravityTRAP plates. After tissue formation, the 3D microtissues were maintained in 3D INSIGHT Human Liver Maintenance Medium-INF (hLiMM CS-07-001b-01; InSphero AG) at 37° C. in a humidified 5% CO2 cell culture incubator for 4 days. Half of the culture medium was replenished every 2 days.

Preparation of Compositions: 2 Components Combination Matrix

For these experiments, a checkerboard matrix was generated. ELA and component (ii) stocks were serially diluted in DMSO in 2-points series in a row (ELA) and a 3-points series in a column (component (ii)) of a 96-well plate. Subsequently, the 2×3 combination matrix was generated by 1:1 mixing of all single agent concentrations.

Metabolic Stimulation of 3D INSIGHT Human Liver Microtissues and Compound Treatment 3D INSIGHT human liver microtissue (InSPhero) were cultured under standard conditions, as described above. Microtissues were then deprived for 24 hours in serum-free medium. For the treatments with ELA, component (ii) and the respective ELA/component (ii) combinations, the serum-deprived microtissues were treated with both a metabolic induction of NASH stimulus and the compounds (Day 0) followed by the renewal of metabolic induction of NASH stimulus at Day 3 for an additional 3 days period. The supernatants for the measurement of Col1α1 were harvested at Day 6.

Col1α1 ELISA

The level of Col1α1 was measured using a Sandwich ELISA. Briefly, the wells of an ELISA plate were first coated with the capture antibody (Mouse Anti-Human Pro-Collagen I α 1 Capture Antibody, "Elisa Pro-Collagen I α1/COLIA1", DuoSet ELISA, R&D, catalog No.: DY6220-05) at RT overnight. After 3 washes in PBS+0.05% Tween 20, a blocking solution consisting of PBS+1% BSA was added for one hour followed by another washing cycle. The culture supernatants were transferred into the wells for binding to the capture antibody for a period of 2 h at room temperature. After the washing procedure, the detection antibody (Biotinylated Sheep Anti-Human Pro-Collagen I α 1 Detection Antibody) was added for 2 hours at room temperature followed by 3 washes. For the detection, an HRP-conjugated Streptavidin was first applied for 20 min at room temperature. After washing, the HRP substrate TMB (BD, #555214) was added and incubated for 20 min at room temperature in the dark. Upon oxidation, TMB forms a water-soluble blue reaction product that becomes yellow with addition of sulfuric acid (solution stop), enabling accurate measurement of the intensity at 450 nm using a spectrophotometer. The developed color is directly proportional to the amount of col1α1 present in the supernatant.

3. Illustration in LPS-Activated Macrophages

Differentiation of THP-1 Monocytes into Macrophages

THP-1 monocytes (ECACC #88081201) were seeded at a density of 25550 cells per well in 384-well plate in RPMI1640 (Gibco, 21875) supplemented with 10% SVF and differentiated into macrophages using PMA (Phorbol 12-myristate 13-acetate, Sigma, P8139) at the final concentration of 100 ng/ml for 24 hours.

Preparation of Compositions: 2 Components Combination Matrix

For these experiments, a checkerboard matrix was generated. ELA and component stocks were serially diluted in DMSO in 6-points series in a column (ELA) and a 10-points series in a raw (component) of a 96-well plate for other compounds. Subsequently, the 6×10 combination matrix was generated by 1:1 mixing of all single agent concentrations.

Compound Treatments and LPS Stimulation

After 24 hrs with PMA, medium was removed, and replaced by serum free RPMI. For the treatments with ELA, component and the respective ELA/component combinations, the serum-deprived THP-1 macrophages were preincubated for 24 hours with the compounds followed by addition of lipopolysaccharide LPS (100 ng/ml, E. coli 055 B5, Sigma, L6529) for an additional 6 hours period.

Human TNFα Quantification

Human TNFα is quantified in the supernatants using the Homogeneous Time Resolved Fluorescence (HTRF) technology (Cisbio 62HTNFAPEG), based on FRET technology. FRET (Fluorescence Resonance Energy Transfer) is based on the transfer of energy between two fluorophores, a donor and an acceptor, when in close proximity. Molecular interactions between biomolecules can be assessed by coupling each partner with a fluorescent label and by detecting the level of energy transfer (665 nm). Cell supernatant, sample or standard were dispensed directly into the assay plate for the detection by HTRF® reagents. The antibodies labeled with the HTRF donor and acceptor were pre-mixed and added in a single dispensing step. Signal intensity is proportional to the number of antigen-antibody complex formed and therefore to the TNFα concentration. Seven points standard curve (from 39 pg/ml to 2500 pg/ml with supplied human TNFα) was obtained by fitting the data with the 4 Parameter Logistic model.

4. Illustration in Fat-Loaded Hepatocytes (HepG2)

HepG2 Culture

The human hepatocyte carcinoma were cultured in DMEM 4.5 g/L glucose (Gibco cat #31053 that was supplemented with 10% fetal bovine serum (FBS, Gibco cat #10270), 1% penicillin/streptomycin (Gibco cat #15140), 1% MEM NEAA (Gibco cat #11140), 1% L-Glutamine (Gibco cat #25030), and 1% Sodium Pyruvate (Gibco cat #11360).

Preparation of Compositions: 2 Components Combination Matrix

For these experiments, a checkerboard matrix was generated. ELA and component stocks were serially diluted in DMSO in 5-points series in a row (ELA) and a 11-points series in a column (component) of a 384-well plate. Subsequently, the 5×11 combination matrix was generated by 1:1 mixing of all single agent concentrations.

Free Fatty Acid (FFA) Preparation

Oleic (#O1383) and palmitic (P0500) acids were purchased at Sigma. FFA stock solutions (100 mM) were prepared in 0.1M NaOH at 80° C. Working solutions of 4.5 mM palmitate/10% bovine serum albumin (BSA) and 9 mM oleate/10% BSA were prepared by complexing an appropriate volume of stock solution to 10% BSA (FFA-free low endotoxin; Sigma-Aldrich, Bornem, Belgium) in a 55° C. water bath (15 min).

Fat Loading and Compound Treatment

HepG2 were plated at a density of 40000 cells/well into 384-well plates to assess lipid droplets content. The next day, cell-culture medium was removed, and cells were washed with PBS (Invitrogen cat #14190). HepG2 were deprived for 24 hours in serum-free medium. For the treatments with ELA, component and the respective ELA/component combinations, the serum-deprived HepG2 were pre-incubated for 24 hours with the compounds followed by the addition of an oleic:palmitic acids mixture (2:1) with a final concentration of 0.5 mM for an additional 24 hours period.

Intra-Cellular Lipid Droplets Measurement

To measure intracellular lipid droplets content, the cells were brought to room temperature and washed with 40 µL PBS. Cells were incubated 30 min at room temperature with 40 µL of diluted Adipored reagent (2.5 µL Adipored reagent per 200 µL PBS) (Lonza, Walkersville, Md.). The relative fluorescence was measured (k excitation at 485 nm, k emission at 580 nm) using a fluorescence spectrometer (Spark Tecan cat #30086376 SN #1801002745). The analyses were performed in quadruplicate.

5. Illustration in 3D Huh7 Spheroid Culture

3D Huh7 Spheroid Culture

Cryopreserved Huh7 were purchased from ECACC. Cells were grown in ULA plates (Costar), William's medium (Sigma) containing 10% FBS (Gibco) at 37° C. in a humidified 5% CO2 cell culture incubator. Cells aggregated and formed spheroids within 5 days.

Preparation of Compositions: 2 Components Combination Matrix

For these experiments, a checkerboard matrix was generated. ELA and component (ii) stocks were serially diluted in DMSO in 2-points series in a row (ELA) and a 3-points series in a column (component (ii)) of a 96-well plate. Subsequently, the 2×3 combination matrix was generated by 1:1 mixing of all single agent concentrations.

Metabolic Stimulation of 3D Huh7 Spheroid Culture and Compound Treatment

3D Huh7 spheroids were cultured under standard conditions, as described above. They were then deprived for 24 hours in serum-free medium. For the treatments with ELA, component (ii) and the respective ELA/component (ii) combinations, the serum-deprived spheroids were treated with both a metabolic NASH stimulus and the compounds (Day 0) followed by the renewal of the metabolic NASH stimulus and the compounds at Day 4 for an additional 3 days period. The spheroids were stained for lipid accumulation at Day 7.

Lipids Staining & Quantification

Intracellular lipid accumulation was quantified using the ADIPORED Assay Reagent (Lonza). Spheroids were subjected to fluorescence assay quantification at λexc: 485 nm and λem: 572 nm, using fluorescence plate reader (TECAN).

Results and Discussion

The abnormal persistence of differentiated myofibroblasts is a characteristic of many fibrotic diseases. Following liver injury, quiescent HSCs undergo a process of activation that is characterized by a differentiation into (α-SMA)-positive myofibroblasts. The PPAR agonist elafibranor has an antifibrotic activity in hHSC activated with the profibrogenic cytokine TGFβ1 (FIG. 9). It is herein surprisingly shown that combinations of MSDC-0602, PXS-4728, Apararenone, CF-102 (Namodenoson), Vismodegib, PBI-4050, emricasan, DUR-928, VK-2809 or KD-025 with elafibranor synergistically inhibited α-SMA production by HSC (FIG. 9).

Since the liver is composed of different cell types (hepatocytes, immune cells, HSC) and as HSC activation can result from different stimuli involving the other hepatic cells, a liver microtissue model was also employed to test combination treatments on fibrosis. Treatment with a metabolic NASH stimulus increased collagen production by the microtissue. In this model, Elafibranor synergized with CP-640186, GS-0976 and Nalmefene to inhibit collagen production (FIG. 10).

Taken together these results show synergistic antifibrotic effects of the combinations of elafibranor with MSDC-0602, PXS-4728, Apararenone, CF-102 (Namodenoson), Vismodegib, PBI-4050, emricasan, DUR-928, VK-2809, KD-025, CP-640186, GS-0976 or Nalmefene (JKB-121).

Metabolic diseases such as NAFLD/NASH are associated with low-grade inflammation. Activation of immune cells produces cytokines that alter the metabolic functions of the liver and peripheral organs (adipose tissue, pancreas). Gut permeability, described in metabolic and hepatic diseases, results in increased circulating bacterial components (lipopolysaccharides or LPS) that activate macrophages in the liver and peripheral organs (adipose tissue). Since PPARs have anti-inflammatory activities, we investigated whether elafibranor and other compounds, could inhibit macrophage activation by LPS. In a model of THP1 monocytes differentiated into macrophages, LPS treatment activates macrophages, as measured by TNFα secretion. Elafibranor (1 µM) alone inhibited TNFα by 21% (FIG. 11). Surprisingly, the combination of elafibranor with gemcabene potently inhibited TNFα secretion by 50% (FIG. 11). Therefore, this result shows the capacity of elafibranor to synergize with other compounds to reduce the inflammatory tone observed in a number of diseases, including NASH and metabolic diseases.

NAFLD/NASH is characterized by primary fat accumulation in hepatocytes (steatosis), which induces lipotoxicity, leading to inflammation, cell death, tissue remodeling and eventually fibrosis. As PPARα and PPARδ are known to induce fat oxidation and inhibit de novo lipogenesis, we wanted to see whether elafibranor combined with other compounds could prevent fat accumulation in hepatocytes. Therefore, HepG2 cells were treated with free fatty acid (FFA) to induce accumulation of lipid droplets. In this model, elafibranor (10 µM) alone reduced fat accumulation by 20%. Unexpectedly, the reduction reached 40% when elafibranor was combined to CP-640186, VK-2809, Apararenone or Aramchol (FIG. 12).

A tridimensional (3D) vitro model of hepatocytes was also employed to address this question, allowing a more physiological reproduction of the liver architecture. In this model, fat accumulation was obtained by treatment with a metabolic NASH stimulus. Elafibranor (3 µM) reduced fat content by 12% (FIG. 13). Combination of elafibranor with MGL-3196 (1 µM) potently reduced hepatocyte lipid content by 28% (FIG. 13), showing a synergistic effect when both drugs were used together.

Taken together, these results show that elafibranor synergizes with CP-640186, VK-2809, Apararenone, Aramchol and MGL-3196, in particular to reduce steatosis.

In conclusion, these results show the capacity of elafibranor to synergize with MSDC-0602, PXS-4728, Apararenone, CF-102 (Namodenoson), Vismodegib, PBI-4050, emricasan, DUR-928, KD-025, CP-640186, GS-0976, Nalmefene (JKB-121), VK-2809, MGL-3196, and Aramchol, in particular to reduce NAFLD.

Example 2: Combination of ELA and OCA

Materials and Methods

Evaluation of Elafibranor, OCA and the combination Elafibranor+OCA in a chronic CDAA+1% cholesterol model (12 weeks).

The preventive effects of Elafibranor alone, OCA alone and the combination of both were assessed in a fibrosing NASH-model of rats fed a CDAA+1% cholesterol diet. 150-175 g male Wistar rats were fed a control (CSAA) diet, CDAA+1% cholesterol diet, or CDAA+1% cholesterol diet supplemented with Elafibranor 1, 3 and 10 mg/kg/day, OCA 10 and 30 mg/kg/day or combined drugs (Elafibranor 1, 3 and 10 mg/kg/day combined to OCA 10 mg/kg/day) for 12 weeks.

The body weight and the food intake were monitored twice per week. On the last day of treatment, rats were sacrificed after a 6 h fasting period. The liver was rapidly excised for biochemical and histological studies.

All animal procedures were performed according to standard protocols and in accordance with the standard recommendations for the proper care and use of laboratory animals.

Histology
Tissue Embedding and Sectioning:

The liver slices were first fixed for 12 hours in formalin 4% solution. Then, the liver pieces were washed 30 minutes in PBS, and dehydrated in ethanol solutions (successive baths at 70, 80, 95 and 100% ethanol). The liver pieces were incubated in three different baths of Xylene (Sigma-Aldrich cat #534056), followed by two baths in liquid paraffin (56° C.). Liver pieces were then put into racks that were gently filled with HISTOWAX to completely cover the tissue.

The paraffin blocks containing the tissue pieces were removed from the racks and stored at room temperature. The liver blocks were cut into 3 μm slices.

Hematoxylin/Eosin Staining

Liver sections were deparaffinized, rehydrated and incubated for 3 minutes in Mayer's Hematoxylin (Microm, cat #F/C0303). Then, the liver sections were rinsed in water and incubated 1 minute in Eosin G (VWR, cat #1.09844.1000). Sections were rinsed in water then dehydrated, and mounted using the CV Mount medium (Leica, cat #14046430011).

Picrosirius Red Staining

Liver sections were deparaffinized, rehydrated and incubated for 15 minutes in a solution of Fast Green FCF 0.1% (Sigma-Aldrich, cat #F7258) before rinsing in a bath of 0.5% acetic acid (Panreac, cat #131008.1611). Then, the liver sections were rinsed in water and incubated 30 minutes in a solution of 0.1% sirius red (Direct Red 80, Fluka cat #43665) in saturated aqueous picric acid (Sigma-Aldrich cat #P6744). Sections were then dehydrated, and mounted using the CV Mount medium (Leica, cat #14046430011).

Histological Examinations

A technician blinded to the source of each liver specimen performed histological examinations. Virtual slides were generated using the Pannoramic 250 scanner from 3D Histech. For each animal, a score summarizing the main histological lesions of NASH was attributed according to the NASH Clinical Research Network (Kleiner 2005, Brunt 1999). Briefly, steatosis, lobular inflammation and hepatocytes ballooning were scored. The NAFLD Activity Score (NAS score) was established for each individual as the unweighted sum of the steatosis (0-3), lobular inflammation (0-3) and the ballooning (0-2) injury grading.

Using Quant Center software (3D Histech, including Pattern Quant and Histo Quant modules), collagen-stained areas were quantified. Briefly, Pattern Quant was used to detect the tissue and measure its surface. Then, Histo Quant was used to detect the stained collagen content and measure its surface, based on a color threshold method. The fibrosis area was then expressed as the percentage of the collagen surface to the whole tissue per animal.

Measurement of Hepatic Collagen Content

The hepatic collagen content was determined using the appropriate QuickZyme kit (Total collagen assay, cat #QZB-totcol2). The assay is based on the detection of hydroxyproline, which is a non-proteinogenic amino acid mainly found in the triple helix of collagen. Thus, hydroxyproline in tissue hydrolysates can be used as a direct measure of the amount of collagen present in the tissue (without discrimination between procollagen, mature collagen and collagen degradation products).

Complete hydrolysis of tissue samples in 6M HCl at 95° C. is required before dosing the hydroxyproline. The assay results in the generation of a chromogen with a maximum absorbance at 570 nm. Results are expressed as mg of collagen/g of liver.

Alpha 2 Macroglobuline ($\alpha$2M)

The plasmatic concentration of $\alpha$2M was determined using the Abcam kit (cat #ab157730), according to the manufacturer's instructions. Briefly, the microplate is pre-coated with an antibody specific for rat $\alpha$ 2M. Standards, controls, and samples are then pipetted into the wells and any $\alpha$ 2M present in the plasma is bound by the immobilized antibody. After washing, a horseradish peroxidase labeled secondary antibody is added to the wells. Following a wash, a substrate solution is added to the wells. The enzyme reaction is stopped by adding the Stop Solution. The intensity of the color measured at 450 nm is proportional to the amount of $\alpha$ 2M bound in the initial step. The sample values are then deduced from the standard curve. Results are expressed in ng/mL.

Procollagen III N-Terminal Propeptide (PIIINP)

The plasmatic concentration of PIIINP was determined using an ELISA assay from Cloud-Clone Corp (cat #SEA573Ra), according to the manufacturer's instructions. The microtiter plate is pre-coated with an antibody specific to PIIINP. Standards or samples are added to the appropriate microtiter plate wells with a biotin-conjugated antibody specific to PIIINP. Next, Avidin conjugated to Horseradish Peroxidase (HRP) is added to each microplate well and incubated. After TMB substrate solution is added, only those wells that contain PIIINP, biotin-conjugated antibody and enzyme-conjugated Avidin will exhibit a change in color. The enzyme-substrate reaction is terminated by the addition of sulphuric acid solution and the color change is measured spectrophotometrically at a wavelength of 450 nm±10 nm. The concentration of PIIINP in the samples is then determined by comparing the OD of the samples to the standard curve. Results are expressed in pg/mL.

Hepatic Gene Expression Analysis

Total RNA was isolated from rat livers using RNeasy Mini Kit (Qiagen) following manufacturer's instructions. Total RNA were reverse transcribed into cDNA using M-MLV RT (Moloney Murine Leukemia Virus Reverse Transcriptase) (Invitrogen cat #28025) in 1×RT buffer (Invitrogen), 0.5 mM DTT (Invitrogen), 0.18 mM dNTPs (Promega), 200 ng pdN6 (Amersham) and 30 U of RNase inhibitor (Promega).

Quantitative PCR was then carried out using the CFX96 TOUCH Real-Time PCR Detection System (Biorad). Briefly, the PCR reactions were performed in 96-WP format in 25 µl of total volume containing 1 µL of reverse transcription reaction, 0.5 µL of reverse and forward primers (10 pmol each), and 12.5 µl of 2×iQ SYBR Green Supermix (BioRad), using the following primer sequences:

| Gene | Forward | Reverse |
|---|---|---|
| RPLP0 | CATGCTCAACATCTCCCCCT TCTCC (SEQ ID NO: 1) | GGGAAGGTGTAATCCGTCTC CACAG (SEQ ID NO: 2) |
| αSMA (ACTA2) | ACTGGGACGACATGGAAAAG (SEQ ID NO: 3) | CATCTCCAGAGTCCAGCACA (SEQ ID NO: 4) |
| TIMP1 | TCCCCAGAAATCATCGAGAC (SEQ ID NO: 5) | TCAGATTATGCCAGGGAACC (SEQ ID NO: 6) |
| TGFB1 | TGAGTGGCTGTCTTTTGACG (SEQ ID NO: 7) | TGGGACTGATCCCATTGATT (SEQ ID NO: 8) |
| CCR5 | CAGAACAGTCAACTTTGGGG (SEQ ID NO: 9) | ACGTGGAAAATGAGGACTGC (SEQ ID NO: 10) |

Expression levels were normalized using the expression of RPLP0 gene as a housekeeping gene of reference in samples. For each gene, the standard curves were drawn by selecting the best points (at least three points) in order to have PCR reaction efficiency close to 100% and a correlation coefficient close to 1. Expression levels were determined using the standard curve equation for both the housekeeping gene and the target gene (taking into account the specific PCR efficiency of each target gene).

Results and Discussion

The results are reported in the following table and in FIGS. 1-5.

| | GFT505 3 mg/kg/d | OCA 10 mg/kg/d | GFT505 + OCA |
|---|---|---|---|
| Fibrosis surface | 34% ± 17%*** | 74% ± 45% | 19% ± 4% # |
| Hepatic collagen content | 45% ± 12%*** | 67% ± 23%** | 34% ± 5% # |
| αSMA mRNA level | 66% ± 27% | 109% ± 68% | 39% ± 18% # |
| TIMP1 mRNA level | 78% ± 23% | 110% ± 43% | 46% ± 13% ## |
| TGFβ1 mRNA level | 94% ± 20% | 110% ± 23% | 67% ± 16% ## |
| CCR5 mRNA level+ | 103% ± 51% | 81% ± 28% | 56% ± 17% # |

Percentage over the untreated CDAA + 1% cholesterol rats
**p < 0.01,
***p < 0.001 vs CDAA + 1% cholesterol group (ANOVA + Bonferroni)
# p < 0.05,
## p < 0.01 vs the best single agent (Student t-test)
(+marker of inflammation)

Western life style is invariably linked with high incidence rate of non-alcoholic steatohepatitis (NASH), a chronic liver disease that often progresses to liver fibrosis and cirrhosis and may ultimately lead to hepatocellular carcinoma. Currently, there is no approved therapy for NASH. Drug combinations directed simultaneously at multiple therapeutic targets have the potential to dramatically improve the drug response and to benefit the widest patient population. Drug combinations were previously tested in other systemic diseases, such as hypertension, dyslipidemia or type 2 diabetes and showed better control of the underlying diseases and decreased the morbidity and the mortality. In recent phase 2B studies, both elafibranor (PPAR α/δ agonist) and OCA (FXR agonist) have shown efficacy on NASH and fibrosis endpoints. We wanted to compare their action on relevant NASH pathology outcomes, and to look for therapeutic benefits of the combination.

To achieve this aim, NASH histology and fibrosis were induced by feeding Wistar rats with a choline-deficient L-amino-acid-defined-diet that was supplemented with cholesterol (CDAA/chol diet). Animals in the intervention groups, received either elafibranor or OCA or both compounds for the entire study period. NASH and fibrosis development were evaluated by histology. Additional biochemical and molecular analyses were also performed on different relevant biomarkers.

Wistar rats fed on the CDAA/chol diet developed NASH-related histology and fibrosis with high penetration of severe disease. Advanced steatosis, lobular inflammation and ballooning were present in all animals and NAS score varied between 6 and 8. Hepatic histology (picrosirius positive area) and biochemistry (hepatic collagen concentration) showed on average a fourfold increase in hepatic fibrosis content and fibrosis score was either 3 or 4 for all the animals on the CDAA/c diet that received no drug treatment. The expression of genes related to inflammation, oxidative stress, tissue remodeling and fibrosis was increased and consistent with gene signatures that were previously reported in NASH patients with severe disease.

Elafibranor and OCA administration alone resulted in a very significant attenuation of fibrosis development. Similar efficacy on fibrosis was observed in animals that received both compounds, although at significantly lower doses. Hepatocyte damage, as judged by ballooning, was prevented or attenuated by elafibranor, in a dose-dependent manner. Instead, OCA has only showed partial ballooning attenuation at the doses that were used in this study. Lobular inflammation was attenuated by elafibranor in a dose-dependent manner and to a lesser extent with OCA. Finally, the administration of either drug candidate alone has partially attenuated the increase of tissue remodeling, inflammation and oxidative stress markers and the combination of both compounds was more efficient as compared to any single agent.

Therefore, it is herein shown that the synergistic action of elafibranor and OCA on liver fibrosis in the CDAA/c diet-induced NASH model produced a comparable therapeutic benefit at significantly lower doses of both drug candidates, as compared to any single agent. From this study, it is credibly expected that doses of both drug candidates can be lowered by a factor of at least 1.5, 2, 2.5 or even at least 3 to obtain the results similar to the initial dose of each compound used individually. In addition, elafibranor showed a clear protective effect on liver damage. The effects of the OCA on ballooning and lobular inflammation were rather modest in this model. From this study, it can be concluded that Elafibranor/OCA combination would benefit a wider patient population and the associated therapeutic dose reduction would decrease the incidence of adverse drug effects.

Example 3: Combination of ELA and CVC

Materials and Methods

Compounds were dissolved in dimethyl sulfoxide (DMSO, Fluka cat #41640). CVC was obtained commercially from CLINISCIENCES (Réf: A13643-10, Batch number: 497223-25-3).

Bezafibrate was synthesized at Genfit.

hHSC Culture

The human primary hepatic stellate cells (hHSC) (Innoprot) were cultured in STeCM medium (ScienCell cat

5301) that was supplemented with 2% fetal bovine serum (FBS, ScienCell cat #0010), 1% penicillin/streptomycin (ScienCell cat #0503) and stellate cell growth supplement (SteCGS; ScienCell cat #5352). Cell-culture flasks were coated with Poly-L Lysine (Sigma cat #P4707) for a better adherence.

Preparation of Compositions

2 Components Combination Matrix (Elafibranor/CVC)

For these experiments, a checkerboard matrix was generated. CVC and Elafibranor stocks were serially diluted in DMSO in a 5-points series in a row (Elafibranor) and a 6-points series in a column (Cenicriviroc) of a 96-well plate. Subsequently, the 6×7 combination matrix was generated by 1:1 mixing of all single agent concentrations. The test concentrations for each compound were chosen based on the respective $IC_{50}$ of each compound as single agent obtained by measuring α-SMA content in the HSC model stimulated with TGF-β1.

Activation of hHSC with TGF-β1 and Compound Treatment

The human primary hepatic stellate cells (hHSC) (Innoprot) were cultured under standard conditions, as described above. The cells were subsequently plated at a density of $2 \times 10^4$ cells/well into 96-well plates for the measure of α-SMA by ELISA.

The next day, cell-culture medium was removed, and cells were washed with PBS (Invitrogen cat #14190). hHSC were deprived for 24 hours in serum-free and SteCGS-free medium. For the treatments with CVC, Elafibranor, Bezafibrate and the pairwise combinations of CVC/Elafibranor and CVC/Bezafibrate, the serum-deprived hHSC were pre-incubated for 1 hour with the compounds followed by addition of the profibrogenic stimuli TGF-β1 (PeproTech cat #100-21, 1 ng/mL) in serum-free and SteCGS-free medium for an additional 48 hour period.

α-SMA ELISA

The level of α-SMA was measured using a Sandwich ELISA. Briefly, the wells of an ELISA plate were first coated with the capture antibody (mouse monoclonal anti-ACTA2, Abnova) at 4° C. overnight. After 3 washes in PBS+0.2% Tween 20, a blocking solution consisting of PBS+0.2% BSA was added for one hour followed by another washing cycle. The cell lysates were transferred into the wells for binding to the capture antibody for a period of 2 h at room temperature. After the washing procedure, the detection antibody (biotinylated mouse monoclonal anti-ACTA2, Abnova) was added for 2 hours at room temperature followed by 3 washes. For the detection, an HRP-conjugated Streptavidin (R&D Systems cat #DY998) was first applied for 30 min at room temperature. After washing, the HRP substrate TMB (BD, #555214) was added and incubated for 7 min at room temperature in the dark. Upon oxidation, TMB forms a water-soluble blue reaction product that becomes yellow with addition of sulfuric acid (solution stop), enabling accurate measurement of the intensity at 450 nm using a spectrophotometer. The developed color is directly proportional to the amount of α-SMA present in the lysate.

Determination of Synergism by Excess Over Bliss (EOB) Method

The values obtained in the α-SMA ELISA assays were first transformed into percentage inhibitions over TGF-β1 control. Then, using these percentage inhibitions, EOB (Excess Over Bliss) was determined to define the synergistic effects of drug combinations. Expected Bliss additivism score (E) was firstly determined by the equation: $E=(A+B)-(A \times B)$ where A and B are the percentage inhibition of Elafibranor (A) (or Bezafibrate) and Cenicriviroc (B) at a given dose. The difference between the Bliss expectation and the observed inhibition of the combined CVC/Elafibranor (or Bezafibrate) at the same dose is the 'Excess over Bliss' score.

Excess over Bliss score=0 indicates that the combination treatment is additive (as expected for independent pathway effects);

Excess over Bliss score>0 indicates activity greater than additive (synergy); and Excess over Bliss score<0 indicates the combination is less than additive (antagonism).

For the combinations Elafibranor+CVC and Bezafibrate+CVC, an additional total Bliss score was calculated by summation of all EOB.

To validate the synergism, the experimental values corresponding to top EOB score for CVC/Elafibranor combination were plotted in a bar graph.

The significance of the observed differences between CVC/Elafibranor or CVC/Bezafibrate over the highest single agent was determined by a student's t-test. [*: $p<0.05$; : $p<0.01$; *: $p<0.001$]

Results and Conclusions:

The abnormal persistence of differentiated myofibroblasts is a characteristic of many fibrotic diseases.

Following liver injury, quiescent HSCs undergo a process of activation that is characterized by a differentiation into (α-SMA)-positive myofibroblasts.

Figure 1:
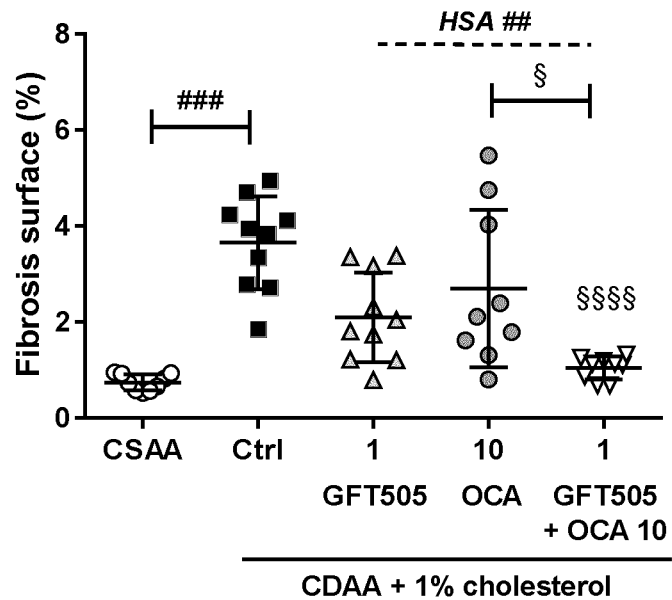
FIG. 1: Effect of the combination of 1 mg/kg/day of ELA and 10 mg/kg/day of OCA on the measure of fibrotic surface.
Figure 2:
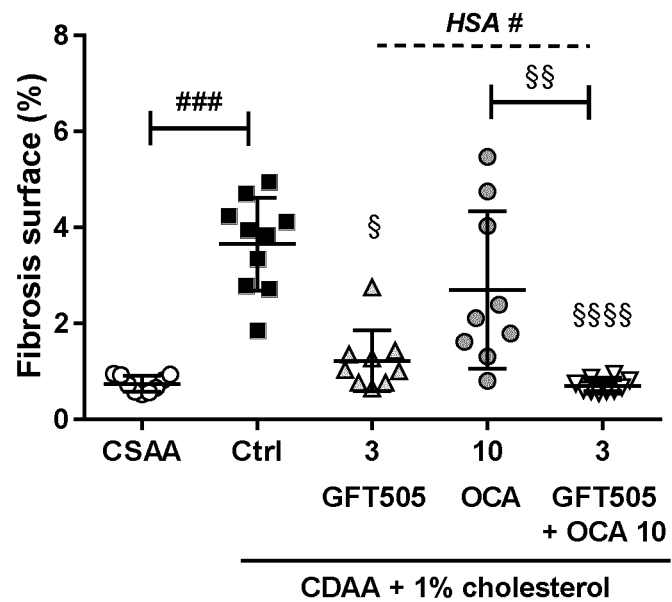
FIG. 2: Effect of the combination of 3 mg/kg/day of ELA and 10 mg/kg/day of OCA on the measure of fibrotic surface.
Figure 3:
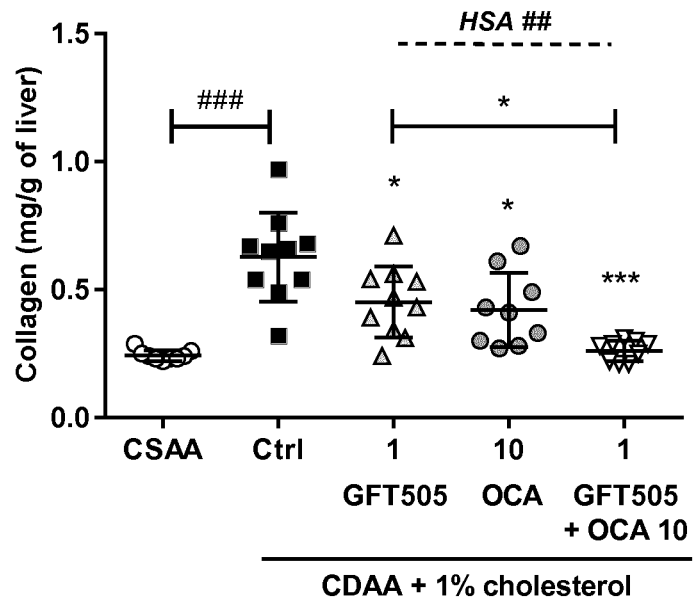
FIG. 3: Effect of the combination of 1 mg/kg/day of ELA and 10 mg/kg/day of OCA on hepatic collagen.
Figure 4:
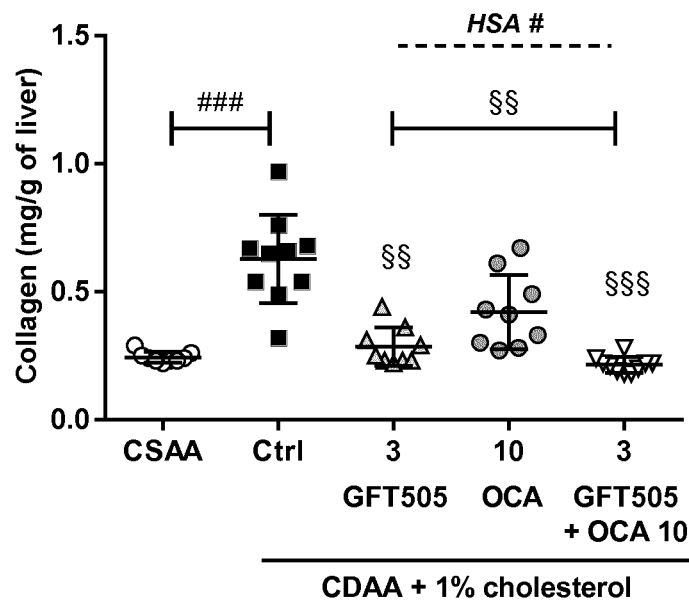
FIG. 4: Effect of the combination of 3 mg/kg/day of ELA and 10 mg/kg/day of OCA on hepatic collagen.
Figure 5:
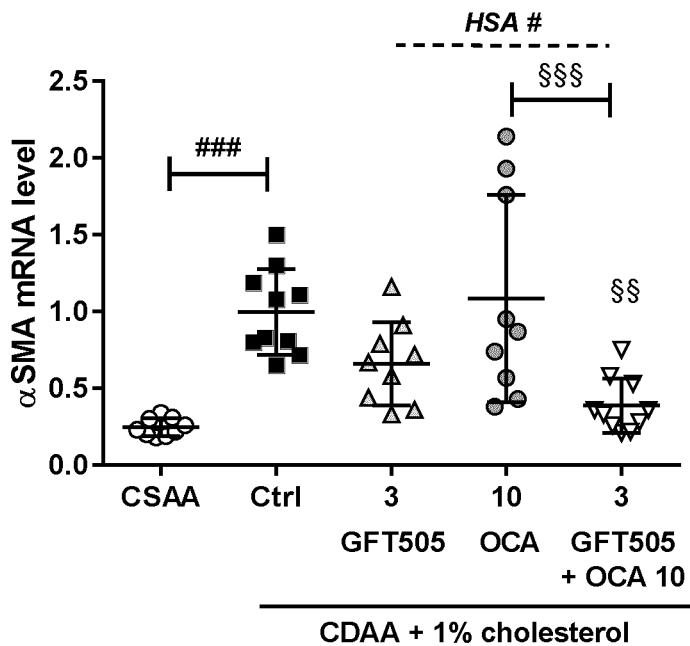
FIG. 5: effect of the combination of 3 mg/kg/day of ELA and 10 mg/kg/day of OCA on fibrosis markers.
Figure 5:
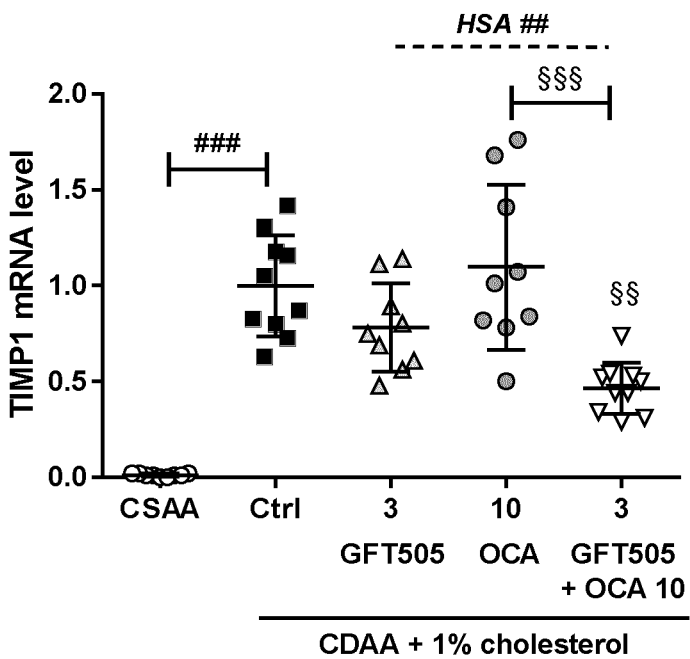
Figure 5:
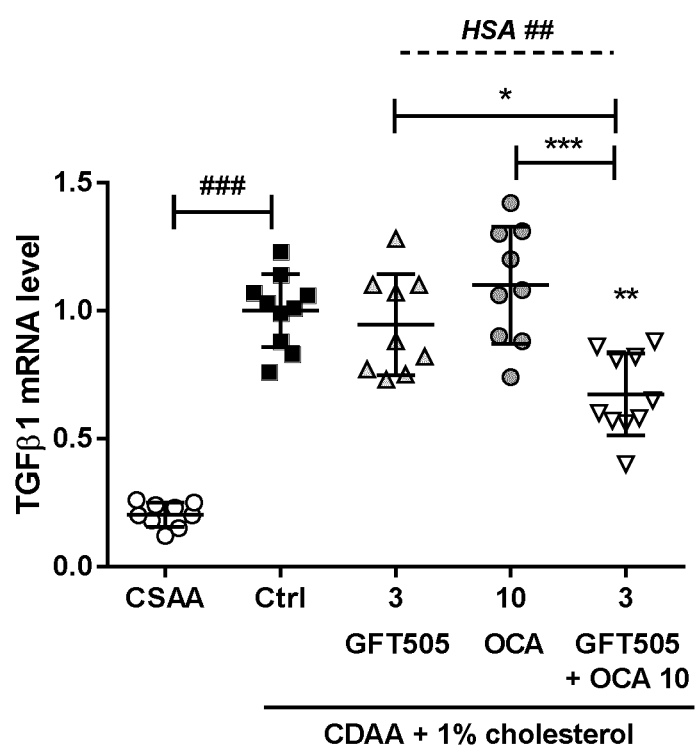
Figure 6:
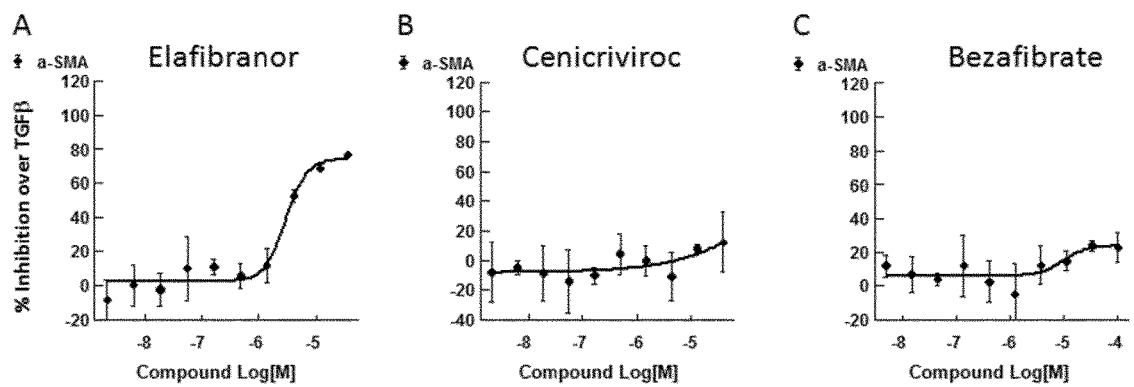
FIG. 6: Differential antifibrotic effect of Elafibranor versus Cenicriviroc, and Bezafibrate in TGFb-induced hHSC.

The PPAR agonist Elafibranor reveals an antifibrotic activity in hHSC activated with the profibrogenic cytokine TGFβ1. The α-SMA marker was reduced by 80% with an $IC_{50}$ of 3.17 µM (FIG. 6A). However, other PPAR agonists like bezafibrate showed a weak antifibrotic profile (FIG. 6C), suggesting that PPAR agonists are not equivalent regarding their antifibrotic properties. CVC alone did not show a significant effect at all doses in TGFβ-activated HSC (FIG. 6B). In order to evaluate if a combination of Elafibranor with CVC could reduce fibrosis in a synergistic manner, combination matrix experiments were performed in TGFβ-induced HSCs. Briefly, CVC and Elafibranor solutions were serially diluted in a checkerboard format generating a 42 combinations matrix covering a large panel of Elafibranor/CVC ratios. Synergy was first determined by calculating Excess Over Bliss scores. These experiments revealed that Elafibranor could synergize with CVC to reduce α-SMA production in activated HSCs (FIGS. 7A and 7B). One of the best example of synergy is shown in FIG. 7C with 5 µM of each compound. Although 5 µM of CVC alone does not show any antifibrotic activity, its addition to 5 µM of Elafibranor could significantly increase in a synergistic manner the activity of Elafibranor and reached up to 60% of inhibition (in comparison to 40% with 5 µM of Elafibranor). In contrast, the combination of CVC with bezafibrate revealed much lower EOB scores (FIGS. 8A and 8B) and none of the combinations gave statistically significant results.

In conclusion, the applicant has discovered unexpected antifibrotic activities for a combination of a ELA and CVC. These results suggest that a combination of a compound of Formula (I) with a CVC can be synergistic and can provide therapeutic benefits in multiple types of diseases such as fibrotic diseases.

Example 4: Combinations of Elafibranor with Selonsertib (SEL), GKT-831 or GS-0976 (GS): Evaluation in a Mouse Fibrosing-NASH Model (8 Weeks)

The preventive effects of the combinations of elafibranor with selonsertib, GKT-831 or GS-0976 were assessed in mice fed a choline-deficient, I-amino acid-defined diet (CDAA) supplemented with 2% cholesterol, 30% milk fat diet and high fructose corn syrup 55 (55% fructose/45% glucose for a final concentration of 42 g/L) in drinking water (Mells et al J Nutr Biochem 2015) (CDFF diet). 5-6 weeks old male C57Bl/6J mice were fed a control (CSAA) diet (n=4), CDFF (n=12), or CDFF supplemented with elafibranor (1 or 3 mg/kg/day), selonsertib (30 mg/kg/day), GKT-831 (60 mg/kg/day) or GS-0976 (10 mg/kg/day) alone or in combination (n=8 per group) for 8 weeks.

The body weight, the food and water intake were monitored twice per week. On the last day of treatment, plasma samples were obtained from retro-orbital blood sampling and mice were sacrificed after a 6 h-fasting period. The liver was rapidly excised for biochemical and histological analyses. All animal procedures were performed according to standard protocols and in accordance with the standard recommendations for the proper care and use of laboratory animals.

Histology
Tissue Embedding and Sectioning

The liver slices were fixed in a formalin 4% solution. Then, the liver pieces were washed 30 minutes in PBS, and dehydrated in ethanol solutions (successive baths at 70, 80, 95 and 100% ethanol). The liver pieces were incubated in three different baths of Xylene (Honeywell cat #534056), followed by two baths in liquid paraffin (59° C.). Liver pieces were then put into racks that were gently filled with HISTOWAX to completely cover the tissue.

The paraffin blocks containing the tissue pieces were removed from the racks and stored at room temperature. The liver blocks were cut into 3 µm slices.
Hematoxylin/Eosin/Safranin Staining Liver sections were deparaffinized, rehydrated and incubated for 3 minutes in Mayer's Hematoxylin (Microm, cat #F/C0303). Then, the liver sections were rinsed in water and incubated 1 minute in a Eosin Y 0.5% alcoholic (VWR, cat #1.02439.0500) and Erythrosin 0.5% solution (VWR, cat #1.15936.0010), and rinsed in with ethanol. Sections were then incubated for 2 minutes in Safranin, and were eventually dehydrated and mounted using the CV Mount medium (Leica, cat #046430011).
Picrosirius Red Staining Liver sections were deparaffinized, rehydrated and incubated for 15 minutes in a solution of Fast Green FCF 0.1% (Sigma-Aldrich, cat #F7258) before rinsing in a bath of 0.5% acetic acid (Panreac, cat #131008.1611). Then, the liver sections were rinsed in water and incubated 30 minutes in a solution of 0.1% sirius red (Direct Red 80, Fluka cat #43665) in saturated aqueous picric acid (Sigma-Aldrich cat #P6744). Sections were then dehydrated, and mounted using the CV Mount medium (Leica, cat #14046430011).
Histological Examinations A technician blinded to the source of each liver specimen performed histological examinations. Virtual slides were generated using the Pannoramic 250 scanner from 3D Histech. For each animal, a score summarizing the main histological lesions of NASH was attributed according to the NASH Clinical Research Network (Kleiner 2005, Brunt 1999). Briefly, steatosis, lobular inflammation and hepatocyte ballooning were scored. The NAFLD Activity Score (NAS) was established for each individual as the unweighted sum of the steatosis (0-3), lobular inflammation (0-3) and the ballooning (0-2) injury grading.

Using Quant Center software (3D Histech, including Pattern Quant and Histo Quant modules), collagen-stained areas were quantified. Briefly, Pattern Quant was used to detect the tissue and measure its surface. Then, Histo Quant was used to detect the stained collagen content and measure its surface, based on a color threshold method. The fibrosis area was then expressed as the percentage of the collagen surface to the whole tissue per animal.

Biochemical Analyses of the Livers
Measurement of Hepatic Collagen Content

The hepatic collagen content was determined using the appropriate QuickZyme kit (Total collagen assay, cat #QZB-totcol2). The assay is based on the detection of hydroxyproline, which is a non-proteinogenic amino acid mainly found in the triple helix of collagen. Thus, hydroxyproline in tissue hydrolysates can be used as a direct measure of the amount of collagen present in the tissue (without discrimination between procollagen, mature collagen and collagen degradation products).

Complete hydrolysis of tissue samples in 6M HCl at 95° C. is required before dosing the hydroxyproline. The assay results in the generation of a chromogen with a maximum absorbance at 570 nm. Results are expressed as mg of collagen/g of liver.
Measurement of Hepatic Triglyceride Content Approximately 100 mg of frozen liver tissue were homogenized with a tissue homogenizer (PRECELLYS24, Bertin Technologies, France) in 150 mM NaCl buffer, containing 15.4 mM NaN3. Lipid fractions in homogenates were extracted with chloroform-methanol (2:1, v/v) followed by measurement of the triglycerides (Biolabo cat #80019).
Plasma Procollagen III N-Terminal Propeptide (PIIINP) Measurement The plasmatic concentration of PIIINP was determined using an ELISA assay from Cloud-Clone Corp (cat #SEA573Mu), according to the manufacturer's instructions. The microtiter plate is pre-coated with an antibody specific to PIIINP. Standards or samples are added to the appropriate microtiter plate wells with a biotin-conjugated antibody specific to PIIINP. Next, Avidin conjugated to Horseradish Peroxidase (HRP) is added to each microplate well and incubated. After TMB substrate solution is added, only those wells that contain PIIINP, biotin-conjugated antibody and enzyme-conjugated Avidin will exhibit a change in color. The enzyme-substrate reaction is terminated by the addition of sulphuric acid solution and the color change is measured spectrophotometrically at a wavelength of 450 nm±10 nm. The concentration of PIIINP in the samples is then determined by comparing the OD of the samples to the standard curve. Results are expressed in pg/mL.
Plasma Tissue Inhibitor of Matrix Metalloproteinases 1 (TIMP-1) Measurement The plasma TIMP-1 levels were measured using a quantitative sandwich ELISA assay from R&D Systems (cat #MTM100) according to the experimental protocol PRO_LIDO_000020. Briefly, a monoclonal antibody specific for mouse TIMP-1 has been pre-coated onto a microplate. Standards, control, and samples are pipetted into the wells and any mouse TIMP-1 present is bound by the immobilized antibody. After washing away any unbound substances, an enzyme-linked polyclonal antibody specific for mouse TIMP-1 is added to the wells. Following a wash to remove any unbound antibody-enzyme reagent, a substrate solution is added to the wells. The enzyme reaction yields a blue product that turns yellow when the Stop Solution is added. The intensity of the color measured is in proportion to the amount of mouse TIMP-1 bound in the initial step. The sample values are then calculated from the standard curve. Results are expressed in pg/ml.

Hepatic Gene Expression Analysis

Total RNA was isolated from mouse livers using RNeasy Mini Kit (Qiagen) following manufacturer's instructions. Total RNA were reverse transcribed into cDNA using M-MLV RT (Moloney Murine Leukemia Virus Reverse Transcriptase) (Invitrogen cat #28025) in 1×RT buffer (Invitrogen), 0.5 mM DTT (Invitrogen), 0.18 mM dNTPs (Promega), 200 ng pdN6 (Amersham) and 30 U of RNase inhibitor (Promega).

Quantitative PCR was then carried out using the CFX96 TOUCH Real-Time PCR Detection System (Biorad). Briefly, the PCR reactions were performed in 96-WP format in 25 µl of total volume containing 1 µL of reverse transcription reaction, 0.5 µL of reverse and forward primers (10 pmol each), and 12.5 µl of 2×iQ SYBR Green Supermix (BioRad), using the following primer sequences:

| Gene | Forward | Reverse |
| --- | --- | --- |
| GAPDH | TATGACTCCACTCACGGCAA (SEQ ID NO: 11) | TCCACGACATACTCAGCACC (SEQ ID NO: 12) |
| Col1α1 | AGGCGAACAAGGTGACAGAG (SEQ ID NO: 13) | GCCAGGAGAACCAGCAGAG (SEQ ID NO: 14) |
| TGFβ1 | TTGCTTCAGCTCCACAGAGA (SEQ ID NO: 15) | TGGTTGTAGAGGGCAAGGAC (SEQ ID NO: 16) |
| CCR2 | TAATATGTTACCTCAGTTCATCCACGG (SEQ ID NO: 17) | TGCTCTTCAGCTTTTTACAGCCTATC (SEQ ID NO: 18) |
| MMP2 | TCCCTAAGCTCATCGCAGAC (SEQ ID NO: 19) | GCTTCCAAACTTCACGCTCT (SEQ ID NO: 20) |
| TNFα | CGTGGAACTGGCAGAAGAGG (SEQ ID NO: 21) | AGACAGAAGAGCGTGGTGGC (SEQ ID NO: 22) |

Expression levels were normalized using the expression of GAPDH gene as a housekeeping gene of reference in samples. For each gene, the standard curves were drawn by selecting the best points (at least three points) in order to have PCR reaction efficiency close to 100% and a correlation coefficient close to 1. Expression levels were determined using the standard curve equation for both the housekeeping gene and the target gene (taking into account the specific PCR efficiency of each target gene).

Results and Conclusions:

In recent clinical studies, elafibranor, selonsertib, GKT-831 and GS-0976 have shown efficacy on NASH and fibrosis endpoints. We wanted to compare their action on relevant NASH pathology outcomes, and to look for therapeutic benefits of the combination. To achieve this aim, NASH was induced by feeding C57Bl/6J mice with a choline-deficient L-amino acid-defined diet supplemented with cholesterol and milk fat, and high fructose corn syrup in drinking water (CDFF diet). Animals in the intervention groups received either elafibranor, selonsertib, GKT-831 or GS-0976 alone or in combination with elafibranor, for the entire study period. NASH development was evaluated by histology and biochemical measurements and hepatic expression of genes involved in pathways relevant for NASH pathology.

CDFF-fed mice developed NASH with high penetration of severe disease. Advanced steatosis and lobular inflammation were present in all animals resulting in a high NAS score of 6 or 7 (FIG. 15-C). The expression of genes related to fibrogenesis, tissue remodeling and inflammation was increased and consistent with gene signatures that were previously reported in NASH patients with severe disease (FIG. 14-E-I).

In this model, elafibranor (3 mg/kg/day) improves NASH histology by reducing steatosis and hepatic lobular inflammation resulting in a global reduction of the NAFLD activity score (not shown). Elafibranor also decreases the expression of genes related to inflammation, tissue remodeling and fibrogenesis (FIG. 14-E-I) resulting in marked reduction of hepatic fibrosis assessed by histology, hepatic collagen content and release of PIIINP and TIMP-1 in the blood (FIG. 14-A-D).

Selonsertib (30 mg/kg/day) alone improved hepatic fibrosis in this model, albeit to a minor extent than elafibranor (FIG. 14). The combination of elafibranor (3 mg/kg/day) and selonsertib (30 mg/kg/day) resulted in a synergistic beneficial effect on hepatic fibrosis (assessed by histology, hepatic collagen content and release of PIIINP and TIMP-1) as well as on hepatic expression of genes involved in fibrogenesis, tissue remodeling and inflammation (FIG. 14).

GKT-831 (60 mg/kg/day) alone had no beneficial effect on NASH and fibrosis in this model. However, when combined to a suboptimal dose of elafibranor (1 mg/kg/day), it reduced hepatic inflammatory infiltrates, the NAFLD activity score and fibrosis (FIG. 15).

Treatment with GS-0976 (30 mg/kg/day) had a mild beneficial effect on liver fat and body weight in this model (FIG. 16). However, the combination with elafibranor at a suboptimal dose (1 mg/kg/day) led to a synergistic effect on whole body fat burning leading to 20% body weight loss and a spectacular decrease in liver steatosis and triglyceride content (FIG. 16).

In conclusion, we found synergistic effects between elafibranor and MSDC-0602, PXS-4728, MT-3995 (Apararenone), CF-102 (Namodenoson), Vismodegib, PBI-4050, Gemcabene, CP-640186, GS-0976, JKB-121 (Nalmefene), VK-2809, MGL-3196, Aramchol, Emricasan, DUR-928 (25-hydroxycholesterol-3-sulfate), Selonsertib, KD-025, or GKT-831.

REFERENCES

Brunt E M et al, 1999, Am J Gastroenterol; 94(9):2467-74
Kleiner D E et al, 2005, Hepatology; 41(6):1313-21

The invention claimed is:

1. A method of delaying, reversing or slowing the progression of a disease, comprising administering to a subject in need of treatment a therapeutically effective amount of a combination product, said combination product comprises:
   (i) elafibranor, a pharmaceutically acceptable salt or a solvate thereof;
   and
   (ii) an anti-NASH, anti-fibrotic or anti-cholestatic agent selected from the group consisting of Selonsertib, GKT-831, PXS-4728A, Aramchol, PBI-4050, MSDC-0602k, VK-2809, MGL-3196, Vismodegib, CF-102 (Namodenoson), MT-3995 (Apararenone), JKB-121 (Nalmefene), emricasan, KD-025, and DUR-928 or a pharmaceutically acceptable salt thereof;
   wherein said disease is selected from the group consisting of liver fibrosis, liver cirrhosis, metabolic liver diseases, non-alcoholic fatty liver disease (NAFLD), non-alcoholic steatohepatitis (NASH), drug-induced liver diseases, alcohol-induced liver diseases, infectious agent induced liver diseases, inflammatory liver diseases, immune system dysfunction-mediated liver diseases, dyslipidemia, cardiovascular diseases, restenosis, syndrome X, metabolic syndrome, diabetes, obesity, hypertension, chronic cholangiopathies, Primary Sclerosing Cholangitis (PSC), Primary Biliary Cholangitis (PBC), biliary atresia, progressive familial intrahepatic cholestasis type 3 (PFIC3), inflammatory bowel diseases, Crohn's disease, ulcerative colitis, liver cancer, hepatocallular carcinoma, gastrointestinal cancer, gastric cancer, colorectal cancer, metabolic disease-induced liver fibrosis or cirrhosis, NAFLD-induced fibrosis or cirrhosis, NASH-induced fibrosis or cirrhosis, alcohol-induced liver fibrosis or cirrhosis, drug-induced liver fibrosis or cirrhosis, infectious agent-induced liver fibrosis or cirrhosis, parasite infection-induced liver fibrosis or cirrhosis, bacterial infection-induced liver fibrosis or cirrhosis, viral infection-induced fibrosis or cirrhosis, HBV-infection induced liver fibrosis or cirrhosis, HCV-infection induced liver fibrosis or cirrhosis, HIV-infection induced liver fibrosis or cirrhosis, dual HCV and HIV-infection induced liver fibrosis or cirrhosis, radiation- or chemotherapy-induced fibrosis or cirrhosis, biliary tract fibrosis, liver fibrosis or cirrhosis due to any chronic cholestatic disease, gut fibrosis of any etiology, Crohn's disease-induced fibrosis, ulcerative colitis-induced fibrosis, small intestine fibrosis, colon fibrosis, stomach fibrosis, lung fibrosis, lung fibrosis consecutive to chronic inflammatory airway diseases, chronic obstructive pulmonary disease (COPD), asthma, emphysema, smoker's lung, tuberculosis, pulmonary fibrosis, and idiopathic pulmonary fibrosis (IPF).

2. The method according to claim 1, wherein component (i) is elafibranor.

3. The method according to claim 1, wherein said combination product does not contain cenicriviroc (CVC) or obeticholic acid (OCA).

* * * * *

SEQUENCE LISTING

<160> NUMBER OF SEQ ID NOS: 22

<210> SEQ ID NO 1
<211> LENGTH: 25
<212> TYPE: DNA
<213> ORGANISM: Artificial Sequence
<220> FEATURE:
<223> OTHER INFORMATION: forward primer

<400> SEQUENCE: 1
catgctcaac atctccccct tctcc                                      25

<210> SEQ ID NO 2
<211> LENGTH: 25
<212> TYPE: DNA
<213> ORGANISM: Artificial Sequence
<220> FEATURE:
<223> OTHER INFORMATION: reverse primer

<400> SEQUENCE: 2
gggaaggtgt aatccgtctc cacag                                      25

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
actgggacga catggaaaag                                            20

<210> SEQ ID NO 4
<211> LENGTH: 20
<212> TYPE: DNA
<213> ORGANISM: Artificial Sequence
<220> FEATURE:
<223> OTHER INFORMATION: reverse primer

<400> SEQUENCE: 4
catctccaga gtccagcaca                                            20

<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
tccccagaaa tcatcgagac                                            20

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
tcagattatg ccagggaacc                                            20

<210> SEQ ID NO 7
<211> LENGTH: 20
<212> TYPE: DNA
<213> ORGANISM: Artificial Sequence
<220> FEATURE:
<223> OTHER INFORMATION: forward primer

<400> SEQUENCE: 7
tgagtggctg tcttttgacg                                            20

<210> SEQ ID NO 8
<211> LENGTH: 20

```
<212> TYPE: DNA
<213> ORGANISM: Artificial Sequence
<220> FEATURE:
<223> OTHER INFORMATION: reverse primer

<400> SEQUENCE: 8
tgggactgat cccattgatt                                                  20

<210> SEQ ID NO 9
<211> LENGTH: 20
<212> TYPE: DNA
<213> ORGANISM: Artificial Sequence
<220> FEATURE:
<223> OTHER INFORMATION: forward primer

<400> SEQUENCE: 9
cagaacagtc aactttgggg                                                  20

<210> SEQ ID NO 10
<211> LENGTH: 20
<212> TYPE: DNA
<213> ORGANISM: Artificial Sequence
<220> FEATURE:
<223> OTHER INFORMATION: reverse primer

<400> SEQUENCE: 10
acgtggaaaa tgaggactgc                                                  20

<210> SEQ ID NO 11
<211> LENGTH: 20
<212> TYPE: DNA
<213> ORGANISM: Artificial Sequence
<220> FEATURE:
<223> OTHER INFORMATION: forward primer

<400> SEQUENCE: 11
tatgactcca ctcacggcaa                                                  20

<210> SEQ ID NO 12
<211> LENGTH: 20
<212> TYPE: DNA
<213> ORGANISM: Artificial Sequence
<220> FEATURE:
<223> OTHER INFORMATION: reverse primer

<400> SEQUENCE: 12
tccacgacat actcagcacc                                                  20

<210> SEQ ID NO 13
<211> LENGTH: 20
<212> TYPE: DNA
<213> ORGANISM: Artificial Sequence
<220> FEATURE:
<223> OTHER INFORMATION: forward primer

<400> SEQUENCE: 13
aggcgaacaa ggtgacagag                                                  20

<210> SEQ ID NO 14
<211> LENGTH: 19
<212> TYPE: DNA
<213> ORGANISM: Artificial Sequence
<220> FEATURE:
<223> OTHER INFORMATION: reverse primer

<400> SEQUENCE: 14
```

| | |
|---|---|
| gccaggagaa ccagcagag | 19 |

<210> SEQ ID NO 15
<211> LENGTH: 20
<212> TYPE: DNA
<213> ORGANISM: Artificial Sequence
<220> FEATURE:
<223> OTHER INFORMATION: forward primer

<400> SEQUENCE: 15

| | |
|---|---|
| ttgcttcagc tccacagaga | 20 |

<210> SEQ ID NO 16
<211> LENGTH: 20
<212> TYPE: DNA
<213> ORGANISM: Artificial Sequence
<220> FEATURE:
<223> OTHER INFORMATION: reverse primer

<400> SEQUENCE: 16

| | |
|---|---|
| tggttgtaga gggcaaggac | 20 |

<210> SEQ ID NO 17
<211> LENGTH: 27
<212> TYPE: DNA
<213> ORGANISM: Artificial Sequence
<220> FEATURE:
<223> OTHER INFORMATION: forward primer

<400> SEQUENCE: 17

| | |
|---|---|
| taatatgtta cctcagttca tccacgg | 27 |

<210> SEQ ID NO 18
<211> LENGTH: 26
<212> TYPE: DNA
<213> ORGANISM: Artificial Sequence
<220> FEATURE:
<223> OTHER INFORMATION: reverse primer

<400> SEQUENCE: 18

| | |
|---|---|
| tgctcttcag cttttttacag cctatc | 26 |

<210> SEQ ID NO 19
<211> LENGTH: 20
<212> TYPE: DNA
<213> ORGANISM: Artificial Sequence
<220> FEATURE:
<223> OTHER INFORMATION: forward primer

<400> SEQUENCE: 19

| | |
|---|---|
| tccctaagct catcgcagac | 20 |

<210> SEQ ID NO 20
<211> LENGTH: 20
<212> TYPE: DNA
<213> ORGANISM: Artificial Sequence
<220> FEATURE:
<223> OTHER INFORMATION: reverse primer

<400> SEQUENCE: 20

| | |
|---|---|
| gcttccaaac ttcacgctct | 20 |

<210> SEQ ID NO 21
<211> LENGTH: 20
<212> TYPE: DNA
<213> ORGANISM: Artificial Sequence

```
<220> FEATURE:
<223> OTHER INFORMATION: forward primer

<400> SEQUENCE: 21
cgtggaactg gcagaagagg                                              20

<210> SEQ ID NO 22
<211> LENGTH: 20
<212> TYPE: DNA
<213> ORGANISM: Artificial Sequence
<220> FEATURE:
<223> OTHER INFORMATION: reverse primer

<400> SEQUENCE: 22
agacagaaga gcgtggtggc                                              20
```